United States Patent
Chene et al.

(10) Patent No.: US 12,364,743 B2
(45) Date of Patent: Jul. 22, 2025

(54) MICROBIOTA SEQUENCE VARIANTS OF TUMOR-RELATED ANTIGENIC EPITOPES

(71) Applicant: ENTEROME S.A., Paris (FR)

(72) Inventors: Laurent Chene, Neuville aux Bois (FR); Alessandra Cervino, Bois-le-Roi (FR); Francesco Strozzi, Paris (FR); Celia Mendez, Charlestown, MA (US); Christophe Bonny, Paris (FR)

(73) Assignee: ENTEROME S.A., Paris (FR)

( * ) Notice: Subject to any disclaimer, the term of this patent is extended or adjusted under 35 U.S.C. 154(b) by 0 days.

(21) Appl. No.: 18/341,337

(22) Filed: Jun. 26, 2023

(65) Prior Publication Data

US 2024/0075117 A1    Mar. 7, 2024

Related U.S. Application Data

(63) Continuation of application No. 16/338,954, filed as application No. PCT/EP2017/075683 on Oct. 9, 2017, now Pat. No. 11,712,465.

(30) Foreign Application Priority Data

Oct. 7, 2016 (EP) .................................. 161929484
Oct. 7, 2016 (EP) .................................. 161929542

(51) Int. Cl.
*A61K 39/00* (2006.01)
*A61P 35/00* (2006.01)
*G01N 33/574* (2006.01)
*G01N 33/68* (2006.01)
*G16B 30/00* (2019.01)
*A61K 39/02* (2006.01)
*C07K 4/04* (2006.01)
*C07K 7/00* (2006.01)

(52) U.S. Cl.
CPC .......... *A61K 39/0011* (2013.01); *A61P 35/00* (2018.01); *G01N 33/574* (2013.01); *G01N 33/6878* (2013.01); *G16B 30/00* (2019.02); *A61K 39/0208* (2013.01); *C07K 4/04* (2013.01); *C07K 7/00* (2013.01); *G01N 2333/195* (2013.01); *G01N 2333/70539* (2013.01)

(58) Field of Classification Search
CPC . A61K 39/0011; A61K 39/0208; A61P 35/00; G01N 33/574; G01N 33/6878; G01N 2333/195; G01N 2333/70539; G16B 30/00; C07K 4/04; C07K 7/00
See application file for complete search history.

(56) References Cited

U.S. PATENT DOCUMENTS

| | | | |
|---|---|---|---|
| 11,712,465 B2 * | 8/2023 | Chene | G01N 33/574 435/7.1 |
| 2007/0087411 A1 | 4/2007 | Sharma et al. | |
| 2008/0166374 A1 | 7/2008 | Debinski et al. | |
| 2011/0110955 A1 | 5/2011 | Debinski et al. | |
| 2012/0052080 A1 | 3/2012 | Okada | |
| 2014/0141044 A1 | 5/2014 | Bhatt et al. | |
| 2018/0078627 A1 | 3/2018 | Zeng et al. | |
| 2018/0133339 A1 | 5/2018 | Derouazi et al. | |
| 2019/0388532 A1 | 12/2019 | Chene et al. | |
| 2020/0025774 A1 | 1/2020 | Chene et al. | |
| 2020/0113983 A1 | 4/2020 | Chene et al. | |
| 2020/0256877 A1 | 8/2020 | Chene et al. | |
| 2021/0106652 A1 | 4/2021 | Chene et al. | |
| 2021/0113678 A1 | 4/2021 | Chene et al. | |
| 2022/0323561 A1 | 10/2022 | Chene et al. | |

FOREIGN PATENT DOCUMENTS

| | | |
|---|---|---|
| CN | 104774261 A | 7/2015 |
| EP | 1587532 A2 | 10/2005 |
| EP | 3536334 A1 | 9/2019 |
| JP | 2006517529 A | 7/2006 |
| JP | 2015518835 A | 7/2015 |

OTHER PUBLICATIONS

Tian et al. (2020). Small and mighty: adaptation of superphylum Patescibacteria to groundwater environment drives their genome simplicity. Microbiome, 8:51.
Cania et al. (2019). A long-term field experiment demonstrates the influence of tillage on the bacterial potential to produce soil structure-stabilizing agents such as exopolysaccharides and lipopolysaccharides. Environmental Microbiome, 14:1.
Dill et al. (2011). Physical limits of cells and proteomes. PNAS, 108(44):17876.
Aglietta et al. (2009). Reduced-intensity allogeneic hematopoietic stem cell transplantation in metastatic colorectal cancer as a novel adoptive cell therapy approach. The European group for blood and marrow transplantation experience. Biol Blood Marrow Transplant, 15:326.
Non-Final Office Action from U.S. Appl. No. 17/823,117 dated Feb. 28, 2024.

(Continued)

*Primary Examiner* — Robert S Cabral
(74) *Attorney, Agent, or Firm* — Harness Dickey & Pierce P.L.C.

(57) ABSTRACT

The present invention relates to cancer immunotherapy, in particular to sequence variants of tumor-related antigenic epitope sequences. Namely, the present invention provides a method for identification of microbiota sequence variants of tumor-related antigenic epitope sequences. Such microbiota sequence variants are useful for the preparation of anticancer medicaments, since they differ from self-antigens and, thus, they may elicit a strong immune response. Accordingly, medicaments comprising microbiota sequence variants, methods of preparing such medicaments and uses of such medicaments are provided.

14 Claims, 3 Drawing Sheets

Specification includes a Sequence Listing.

(56) References Cited

OTHER PUBLICATIONS

Fichtner-Feigl et al., "IL-13 signaling through the IL-13alpha2 receptor is involved in induction of TGF-beta1 production and fibrosis," Nature Medicine, 12(1): 99-106 (2006).
Hirsova et al., "Emerging Roles of T Cells in the Pathogenesis of Nonalcoholic Steatohepatitis and Hepatocellular Carcinoma," Front. Endocrinol. 12(760860): 1-14 (2021).
Office action issued in U.S. Appl. No. 17/043,197 dated Jun. 1, 2023.
Dosset et al. (2012). Universal cancer peptide-based therapeutic vaccine breaks tolerance against telomerase and eradicates established tumor. Clinical Cancer Res., 18(22): 6284-95.
Flugel and Fischer (2014). Simian Virus Tumor Antigen: A virus-specific and preexisting cell protein. Journal of the National Cancer Institute, 55(4): 899-901.
Restriction Requirement issued in U.S. Appl. No. 16/753,657 dated Aug. 9, 2023.
Office Action issued in U.S. Appl. No. 17/929,063 dated Nov. 9, 2023.
Office Action issued in Chinese Application No. CN201880065726.X dated Jan. 20, 2023.
Search Report issued in Chinese Application No. 201880065726.X dated Jan. 17, 2023.
Office Action from U.S. Appl. No. 17/043,197 dated Jan. 16, 2024.
Attallah et al. (2016) Interferon-gamma is associated with hepatic dysfunction in fibrosis, cirrhosis, and hepatocellular carcinoma. J Immunoassay Immunochem, 37(6): 597-610.
Office Action from U.S. Appl. No. 16/753,657 dated Jan. 19, 2024.
Baylot, V., et al., "Chapter 13: TCTP Has a Crucial Role in the Different Stages of Prostate Cancer Malignant Progression," Springer International Publishing AG, 2017, p. 255-261.
Badri, H., et al., "Optimization of radiation dosing schedules for proneural glioblastoma," J. Math. Biol., 72: 1301-1336 (2016).
Office Action from corresponding Russian Application No. 2020135927 dated Jun. 16, 2023.
Office Action from Japanese Application No. 2023-191203 dated Nov. 26, 2024.

\* cited by examiner

MICROBIOTA SEQUENCE VARIANTS OF TUMOR-RELATED ANTIGENIC EPITOPES

PRIORITY STATEMENT

This application is a continuation application of U.S. application Ser. No. 16/338,954 filed on 2 Apr. 2019, which is a national stage application under 35 U.S.C. § 371 of PCT International Application No. PCT/EP2017/075683, which has an international filing date of 9 Oct. 2017 and claims priority under 35 U.S.C. § 119 to European Patent Application Nos. 16192954.2 and 16192948.4 both filed on 7 Oct. 2016. The contents of each application recited above are incorporated herein by reference in their entirety.

FIELD

The present invention relates to the field of cancer immunotherapy, in particular to a method of identification of bacterial sequence variants of epitopes of human tumor-related antigens in the human microbiome. The present invention also relates to methods of providing vaccines comprising such bacterial sequence variants of the human microbiome and to such vaccines. Moreover, the present invention also provides a method for treating a human individual with such vaccines.

BACKGROUND

Cancer is one of the leading causes of death across the world. According to the World Health Organization, in 2012 only, 14 million new cases and 8.2 million cancer-related deaths were reported worldwide, and it is expected that the number of new cancer cases will rise by about 70% within the next two decades. So far, more than 60% of world's total new annual cases occur in Africa, Asia and Central and South America. These regions also account for 70% of the world's cancer deaths. Among men, the five most common sites of cancer are lung, prostate, colorectum, stomach and liver; while in women, those are breast, colorectum, lung, cervix, and stomach.

Cancer has long been managed with surgery, radiation therapy, cytotoxic chemotherapy, and endocrine manipulation, which are typically combined in sequential order so as to best control the disease. However, major limitations to the true efficacy of these standard therapies are their imprecise specificity which leads to the collateral damage of normal tissues incurred with treatment, a low cure rate, and intrinsic drug resistance.

In the last years, there has been a tremendous increase in the development of cancer therapies due notably to great advances in the expression profiling of tumors and normal cells, and recent research and first clinical results in immunotherapy, or molecular targeted therapy, have started to change our perception of this disease.

Promising anticancer immunotherapies have now become a reality and evidences that the host immune system can recognize tumor antigens have led to the development of anticancer drugs which are now approved by regulatory agencies as the US Food and Drug Administration (FDA) and European Medicines Agency (EMA). Various therapeutic approaches include, among others, adoptive transfer of ex vivo expanded tumor-infiltrating lymphocytes, cancer cell vaccines, immunostimulatory cytokines and variants thereof, Pattern recognition receptor (PRR) agonists, and immunomodulatory monoclonal antibodies targeting tumor antigens or immune checkpoints (Galuzzi L. et al., Classification of current anticancer immunotherapies. Oncotarget. 2014 Dec. 30; 5(24):12472-508):

Unfortunately, a significant percentage of patients can still present an intrinsic resistance to some of these immunotherapies or even acquire resistance during the course of treatment. For example, the three-year survival rate has been reported to be around 20% with the anti-CTLA-4 antibody Ipilumumab in unresectable or metastatic melanoma (Snyder et al., Genetic basis for clinical response to CTLA-4 blockade in melanoma. N Engl J Med. 2014 Dec. 4; 371 (23):2189-2199; Schadendorf D et al., Pooled Analysis of Long-Term Survival Data from Phase II and Phase III Trials of Ipilimumab in Unresectable or Metastatic Melanoma. J Clin Oncol. 2015 Jun. 10; 55(17):1889-94), while the three-year survival rate with another check point inhibitor, Nivolumab targeting PD1, has been reported to be of 44% in renal cell carcinoma (RCC) and 18% in NSCLC (McDermott et. al., Survival, Durable Response, and Long-Term Safety in Patients With Previously Treated Advanced Renal Cell Carcinoma Receiving Nivolumab. J Clin Oncol. 2015 Jun. 20; 33(18):2013-20; Gettinger et al., Overall Survival and Long-Term Safety of Nivolumab (Anti-Programmed Death 1 Antibody, BMS-936558, ONO-45 ms) in Patients With Previously Treated Advanced Non-Small-Cell Lung Cancer. J Clin Oncol. 2015 Jun. 20; 33(18):2004-12).

Fundamental drug resistance thus represents a fixed barrier to the efficacy of these immunotherapies. It is thus clear that a different approach to cancer treatment is needed to break this barrier.

Absence of response in a large number of subjects treated with these immunotherapies might be associated with a deficient anti-tumor immune response (as defect in antigen presentation by APC or antigen recognition by T cells). In other words, positive response to immunotherapy correlates with the ability of the immune system to develop specific lymphocytes subsets able to recognize MHC class I-restricted antigens that are expressed by human cancer cells (Kvistborg et. al., Human cancer regression antigens. Curr Opin Immunol. 2013 April; 25(2):284-90).

This hypothesis is strongly supported by data demonstrating that response to adoptive transfer of tumor-infiltrating lymphocytes, is directly correlated with the numbers of CD8+ T-cells transfused to the patient (Besser et al., Adoptive transfer of tumor-infiltrating lymphocytes in patients with metastatic melanoma: intent-to-treat analysis and efficacy after failure to prior immunotherapies. Clin Cancer Res. 2013 Sep. 1; 19(17):4792-800).

A potent anti-tumoral response will thus depend on the presentation of immunoreactive peptides and the presence of a sufficient number of reactive cells "trained" to recognize these antigens.

Tumor antigen-based vaccination represent a unique approach to cancer therapy that has gained considerable interest as it can enlist the patient's own immune system to recognize, attack and destroy tumors, in a specific and durable manner. Tumor cells are indeed known to express a large number of peptide antigens susceptible to be recognized by the immune system. Vaccines based on such antigens thus provide great opportunities not only to improve patient's overall survival but also for the monitoring of immune responses and the preparation of GMP-grade product thanks to the low toxicity and low molecular weight of tumor antigens. Examples of tumor antigens include, among others, by-products of proteins transcribed from normally silent genes or overexpressed genes and from proteins expressed by oncovirus (Kvistborg et al., Curr Opin Immunol. 2013 April; 25(2):284-90) and neo-antigens, resulting from point mutations of cellular proteins. The later are of particular interest as they have been shown to be directly associated with increased overall survival in patient treated with CTLA4 inhibitors (Snyder et al., Genetic basis for clinical response to CTLA-4 blockade in melanoma. N Engl J Med. 2014 Dec. 4; 371(23):2189-2199; Brown et al., Neo-antigens predicted by tumor genome meta-analysis correlate with increased patient survival. Genome Res. 2014 May; 24(5):743-50).

However, most of the tumor-associated antigens (TAAs) and tumor-specific antigens (TSAs) are (existing) human proteins and are, thus, considered as self-antigens. During thymic selection process, T cells that recognize peptide/self MHC complexes with sufficient affinity are clonally depleted. By offering a protection against auto-immune disease, this mechanism of T cell repertoire selection also reduce the possibility to develop immunity against tumor-associated antigens (TAAs) and tumor-specific antigens (TSAs). This is exemplified by the fact that cancer-reactive TCRs are generally of weak affinity. Furthermore, until now, most of the vaccine trials performed with selected tumor-associated antigens (TAAs) and tumor-specific antigens (TSAs) with high binding affinity for MHC have not been shown to elicit strong immunity, probably reflecting the consequence of thymic selection.

Accordingly, the number of human tumor antigens on which cancer vaccines can be developed is limited. Moreover, antigens derived from mutated or modified self-proteins may induce immune tolerance and/or undesired auto-immunity side effects.

There is thus a need in the art to identify alternative cancer therapeutics, which can overcome the limitations encountered in this field, notably resistance to immunotherapies that are currently available.

BRIEF DESCRIPTION OF THE DRAWINGS

In the following a brief description of the appended figures will be given. The figures are intended to illustrate the present invention in more detail. However, they are not intended to limit the subject matter of the invention in any way.

Figure 1:
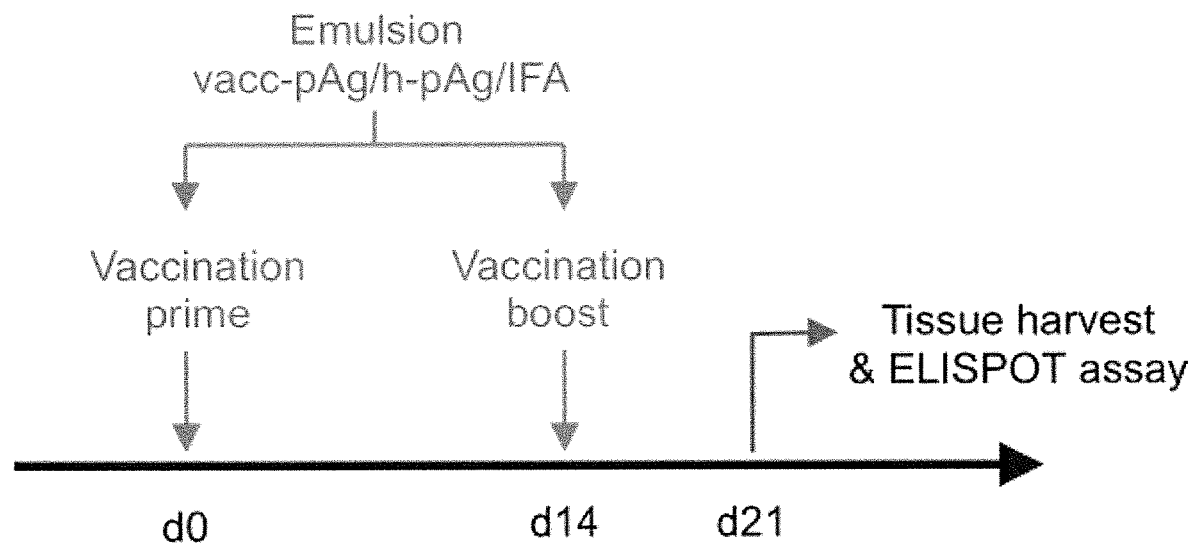

FIG. 1 shows a schematic overview of the immunization scheme used in Examples 5 and 6.

DETAILED DESCRIPTION

Figure 2:
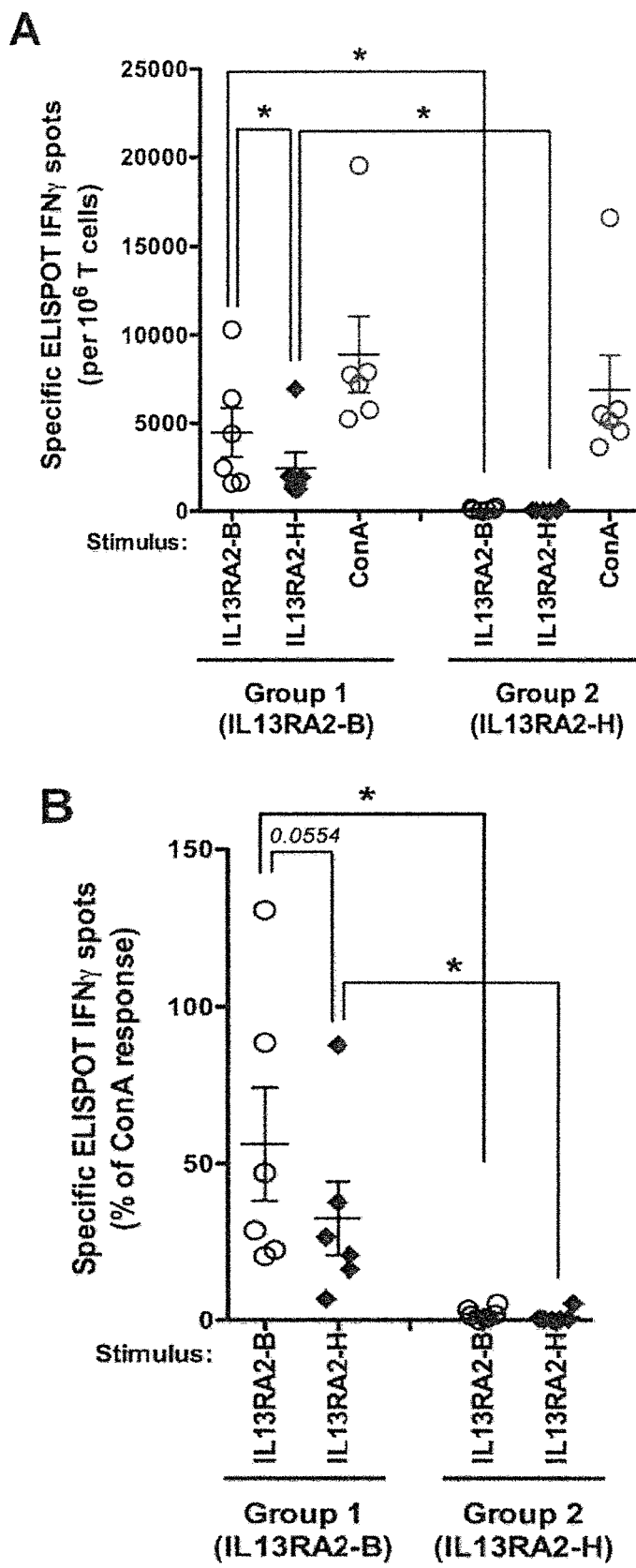
FIG. 2 shows for Example 5 the ELISPOT-IFNγ results for group 1 (IL13RA2-B) and group 2 (IL13RA2-A). The peptide used for vaccination (in between brackets under each group) and the stimulus used in the ELISPOT culture (X-axis) are indicated on the graphs. (A) Number of specific ELISPOT-IFNγ spots (medium condition subtracted). Each dot represents the average value for one individual/mouse from the corresponding condition quadruplicate. (B) For each individual, the level of specific ELISPOT-IFNγ response is compared to the ConA stimulation (value: 100%). Statistical analysis: paired t-test for intra-group comparison and unpaired t-test for inter-group comparison; *p<0.05.

In view of the above, it is the object of the present invention to overcome the drawbacks of current cancer immunotherapies outlined above and to provide a method for identification of sequence variants of epitopes of human tumor-related antigens. In particular, it is the object of the present invention to provide a method to identify bacterial proteins in the human microbiome, which are a source of sequence variants of tumor-related antigen epitopes. Moreover, it is an object of the present invention to provide a method to identify peptides from these bacterial proteins that can be presented by specific MHC molecules.

These objects is achieved by means of the subject-matter set out below and in the appended claims.

Although the present invention is described in detail below, it is to be understood that this invention is not limited to the particular methodologies, protocols and reagents described herein as these may vary. It is also to be understood that the terminology used herein is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Throughout this specification and the claims which follow, unless the context requires otherwise, the term "comprise", and variations such as "comprises" and "comprising", will be understood to imply the inclusion of a stated member, integer or step but not the exclusion of any other non-stated member, integer or step. The term "consist of" is a particular embodiment of the term "comprise", wherein any other non-stated member, integer or step is excluded. In the context of the present invention, the term "comprise" encompasses the term "consist of". The term "comprising" thus encompasses "including" as well as "consisting" e.g., a composition "comprising" X may consist exclusively of X or may include something additional e.g., X+Y.

The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. No language in the specification should be construed as indicating any non-claimed element essential to the practice of the invention.

The word "substantially" does not exclude "completely" e.g., a composition which is "substantially free" from Y may be completely free from Y. Where necessary, the word "substantially" may be omitted from the definition of the invention.

The term "about" in relation to a numerical value x means x±10%.

Method for Identification of Bacterial Sequence Variants Oftumor-Related Antigenic Epitopes The present invention is based on the surprising finding that bacterial proteins found in the human microbiome contain peptides, which are sequence variants of epitopes of human tumor-related antigens. Accordingly, the present inventors found "epitope mimicry" of human tumor-related epitopes in the human microbiome. Interestingly, such epitope mimicry offers a possible way to bypass the repertoire restriction of human T cells due to clonal depletion of T cells recognizing self-antigens. In particular, antigens/epitopes distinct from self-antigens, but sharing sequence similarity with the self-antigen, (i) can still be recognized due to the cross-reactivity of the T-cell receptor (see, for example, Degauque et al., Cross-Reactivity of TCR Repertoire: Current Concepts, Challenges, and Implication for Allotransplantation. Frontiers in Immunology. 2016; 7:89. doi:10.5589/fimmu.2016.00089; Nelson et al., T cell receptor cross-reactivity between similar foreign and self peptides influences naive cell population size and autoimmunity. Immunity. 2015 Jan. 20; 42(1):95-107); and (ii) it is expected that such antigens/epitopes are recognized by T cell/TCR that have not been depleted during T cell education process. Accordingly, such antigens/epitopes are able to elicit a strong immune response leading to clonal expansion of T cell harboring potential cross reactivity with self-antigens. This mechanism is currently proposed to explain part of autoimmune diseases.

The human microbiome, which is composed of thousands of different bacterial species, is a large source of genetic diversity and potential antigenic components. The gut can be considered as the largest area of contact and exchange with microbiota. As a consequence, the gut is the largest immune organ in the body. Specialization and extrathymic T cell maturation in the human gut epithelium is known now for more than a decade. The gut contains a large panel of immune cells that could recognize our microbiota and which are tightly controlled by regulatory mechanisms.

According to the present invention, the large repertoire of bacterial species existing in the gut provides an incredible source of antigens with potential similarities with human tumor antigens. These antigens are presented to specialized cells in a complex context, with large amount of co-signals delivered to immune cells as TLR activators. As a result, microbiota may elicit full functional response and drive maturation of large T memory subset or some time lead to full clonal depletion or exhaustion. Identification of bacterial components sharing similarities with human tumor antigens will provides a new source for selection of epitopes of tumor-related antigens, which (i) overcome the problem of T cell depletion and (ii) should have already "primed" the immune system in the gut, thereby providing for stronger immune responses as compared to antigens of other sources and artificially mutated antigens/epitopes.

In a first aspect the present invention provides a method for identification of a microbiota sequence variant of a tumor-related antigenic epitope sequence, the method comprising the following steps:

(i) selection of a tumor-related antigen of interest,
(ii) identification of at least one epitope comprised in the tumor-related antigen selected in step (i) and determination of its sequence, and
(iii) identification of at least one microbiota sequence variant of the epitope sequence identified in step (ii).

Furthermore, the present invention in particular also provides a method for identification of a microbiota sequence variant of a tumor-related antigenic epitope, the method comprising the following steps:

(1) comparing microbiota sequences with sequences of tumor-related antigenic epitopes and identifying a microbiota sequence variant of a tumor-related antigenic epitope; and
(2) optionally, determining the tumor-related antigen comprising the tumor-related antigenic epitope to which the microbiota sequence variant was identified in step (1).

The terms "microbiota sequence variant" and "tumor-related antigenic epitope sequence" (also referred to as "epitope sequence"), as used herein, refer (i) to a (poly)peptide sequence and (ii) to a nucleic acid sequence. Accordingly, the "microbiota sequence variant" may be (i) a (poly)peptide or (ii) a nucleic acid molecule. Accordingly, the "tumor-related antigenic epitope sequence" (also referred to as "epitope sequence") may be (i) a (poly)peptide or (ii) a nucleic acid molecule. Preferably, the microbiota sequence variant is a (poly)peptide. Accordingly, it is also preferred that the tumor-related antigenic epitope sequence (also referred to as "epitope sequence") is a (poly)peptide.

In contrast to the term "epitope sequence", which may refer herein to peptide or nucleic acid level, the term "epitope", as used herein, in particular refers to the peptide. As used herein, an "epitope" (also known as "antigenic determinant"), is the part (or fragment) of an antigen that is recognized by the immune system, in particular by antibodies, T cell receptors, and/or B cell receptors. Thus, one antigen has at least one epitope, i.e. a single antigen has one or more epitopes. An "antigen" typically serves as a target for the receptors of an adaptive immune response, in particular as a target for antibodies, T cell receptors, and/or B cell receptors. An antigen may be (i) a peptide, a polypeptide, or a protein, (ii) a polysaccharide, (iii) a lipid, (iv) a lipoprotein or a lipopeptide, (v) a glycolipid, (vi) a nucleic acid, or (vii) a small molecule drug or a toxin. Thus, an antigen may be a peptide, a protein, a polysaccharide, a lipid, a combination thereof including lipoproteins and glycolipids, a nucleic acid (e.g. DNA, siRNA, shRNA, antisense oligonucleotides, decoy DNA, plasmid), or a small molecule drug (e.g. cyclosporine A, paclitaxel, doxorubicin, methotrexate, 5-aminolevulinic acid), or any combination thereof. In the context of the present invention, the antigen is typically selected from (i) a peptide, a polypeptide, or a protein, (ii) a lipoprotein or a lipopeptide and (iii) a glycoprotein or glycopeptide; more preferably, the antigen is a peptide, a polypeptide, or a protein.

The term "tumor-related antigen" (also referred to as "tumor antigen") refers to antigens produced in tumor cells and includes tumor associated antigens (TAAs) and tumor specific antigens (TSAs). According to classical definition, Tumor-Specific Antigens (TSA) are antigens present only in/on tumor cells and not in/on any other cell, whereas Tumor-Associated Antigens (TAA) are antigens present in/on tumor cells and non-tumor cells ("normal" cells). Tumor-related antigens are often specific for (or associated with) a certain kind of cancer/tumor.

In the context of the present invention, i.e. throughout the present application, the terms "peptide", "polypeptide", "protein" and variations of these terms refer to peptides, oligopeptides, polypeptides, or proteins comprising at least two amino acids joined to each other preferably by a normal peptide bond, or, alternatively, by a modified peptide bond, such as for example in the cases of isosteric peptides. In particular, the terms "peptide", "polypeptide", "protein" also include "peptidomimetics" which are defined as peptide analogs containing non-peptidic structural elements, which peptides are capable of mimicking or antagonizing the biological action(s) of a natural parent peptide. A peptidomimetic lacks classical peptide characteristics such as enzymatically scissile peptide bonds. In particular, a peptide, polypeptide or protein can comprise amino acids other than the 20 amino acids defined by the genetic code in addition to these amino acids, or it can be composed of amino acids other than the 20 amino acids defined by the genetic code. In particular, a peptide, polypeptide or protein in the context of the present invention can equally be composed of amino acids modified by natural processes, such as post-translational maturation processes or by chemical processes, which are well known to a person skilled in the art. Such modifications are fully detailed in the literature. These modifications can appear anywhere in the polypeptide: in the peptide skeleton, in the amino acid chain or even at the carboxy- or amino-terminal ends. In particular, a peptide or polypeptide can be branched following an ubiquitination or be cyclic with or without branching. This type of modification can be the result of natural or synthetic post-translational processes that are well known to a person skilled in the art. The terms "peptide", "polypeptide", "protein" in the context of the present invention in particular also include modified peptides, polypeptides and proteins. For example, peptide, polypeptide or protein modifications can include acetylation, acylation, ADP-ribosylation, amidation, covalent fixation of a nucleotide or of a nucleotide derivative, covalent fixation of a lipid or of a lipidic derivative, the covalent fixation of a phosphatidylinositol, covalent or non-covalent cross-linking, cyclization, disulfide bond formation, demethylation, glycosylation including pegylation, hydroxylation, iodization, methylation, myristoylation, oxidation, proteolytic processes, phosphorylation, prenylation, racemization, seneloylation, sulfatation, amino acid addition such as arginylation or ubiquitination. Such modifications are fully detailed in the literature (Proteins Structure and Molecular Properties (1993) 2nd Ed., T. E. Creighton, New York; Post-translational Covalent Modifications of Proteins (1983) B. C. Johnson, Ed., Academic Press, New York; Seifter et al. (1990) Analysis for protein modifications and nonprotein cofactors, Meth. Enzymol. 182: 626-646 and Rattan et al., (1992) Protein Synthesis: Post-translational Modifications and Aging, Ann NY Acad Sci, 663: 48-62). Accordingly, the terms "peptide", "polypeptide", "protein" preferably include for example lipopeptides, lipoproteins, glycopeptides, glycoproteins and the like.

In a particularly preferred embodiment, the microbiota sequence variant according to the present invention is a "classical" (poly)peptide, whereby a "classical" (poly)peptide is typically composed of amino acids selected from the 20 amino acids defined by the genetic code, linked to each other by a normal peptide bond.

Nucleic acids preferably comprise single stranded, double stranded or partially double stranded nucleic acids, preferably selected from genomic DNA, cDNA, RNA, siRNA, antisense DNA, antisense RNA, ribozyme, complementary RNA/DNA sequences with or without expression elements, a mini-gene, gene fragments, regulatory elements, promoters, and combinations thereof. Further preferred examples of nucleic acid (molecules) and/or polynucleotides include, e.g., a recombinant polynucleotide, a vector, an oligonucleotide, an RNA molecule such as an rRNA, an mRNA, or a tRNA, or a DNA molecule as described above. It is thus preferred that the nucleic acid (molecule) is a DNA molecule or an RNA molecule; preferably selected from genomic DNA; cDNA; rRNA; mRNA; antisense DNA; antisense RNA; complementary RNA and/or DNA sequences; RNA and/or DNA sequences with or without expression elements, regulatory elements, and/or promoters; a vector; and combinations thereof.

Accordingly, the term "microbiota sequence variant" refers to a nucleic acid sequence or to a (poly)peptide sequence found in microbiota, i.e. of microbiota origin (once the sequence was identified in microbiota, it can usually also be obtained by recombinant measures well-known in the art). A "microbiota sequence variant" may refer to a complete (poly)peptide or nucleic acid found in microbiota or, preferably, to a fragment of a (complete) microbiota (poly)peptide/protein or nucleic acid molecule having a length of at least 5 amino acids (15 nucleotides), preferably at least 6 amino acids (18 nucleotides), more preferably at least 7 amino acids (21 nucleotides), and even more preferably at least 8 amino acids (24 nucleotides). For example, the "microbiota sequence variant" may be a fragment of a microbiota protein/nucleic acid molecule, the fragment having a length of 9 or 10 amino acids (27 or so nucleotides). Preferably, the microbiota sequence variant is a fragment of a microbiota protein as described above. Preferably, the microbiota sequence variant has a length of 8-12 amino acids (as peptide; corresponding to 24-56 nucleotides as nucleic acid molecule), more preferably the microbiota sequence variant has a length of 8-10 amino acids (as peptide; corresponding to 24-30 nucleotides as nucleic acid molecule). Peptides having such a length can bind to MHC (major histocompatibility complex) class I (MHC I), which is crucial for a cytotoxic T-lymphocyte (CTL) response. It is also preferred that the microbiota sequence variant has a length of 13-24 amino acids (as peptide; corresponding to 39-72 nucleotides as nucleic acid molecule). Peptides having such a length can bind to MHC (major histocompatibility complex) class II (MHC II), which is crucial for a CD4+ T-cell (T helper cell) response.

The term "microbiota", as used herein, refers to commensal, symbiotic and pathogenic microorganisms found in and on all multicellular organisms studied to date from plants to animals. In particular, microbiota have been found to be crucial for immunologic, hormonal and metabolic homeostasis of their host. Microbiota include bacteria, archaea, protists, fungi and viruses. Accordingly, the microbiota sequence variant is preferably selected from the group consisting of bacterial sequence variants, archaea sequence variants, protist sequence variants, fungi sequence variants and viral sequence variants. More preferably, the microbiota sequence variant is a bacterial sequence variant or an archaea sequence variant. Most preferably, the microbiota sequence variant is a bacterial sequence variant.

Anatomically, microbiota reside on or within any of a number of tissues and biofluids, including the skin, conjunctiva, mammary glands, vagina, placenta, seminal fluid, uterus, ovarian follicles, lung, saliva, oral cavity (in particular oral mucosa), and the gastrointestinal tract, in particular the gut. In the context of the present invention the microbiota sequence variant is preferably a sequence variant of microbiota of the gastrointestinal tract (microorganisms residing in the gastrointestinal tract), more preferably a sequence variant of microbiota of the gut (microorganisms residing in the gut). Accordingly, it is most preferred that the microbiota sequence variant is a gut bacterial sequence variant (i.e. a sequence variant of bacteria residing in the gut).

While microbiota can be found in and on many multicellular organisms (all multicellular organisms studied to date from plants to animals), microbiota found in and on mammals are preferred. Mammals contemplated by the present invention include for example human, primates, domesticated animals such as cattle, sheep, pigs, horses, laboratory rodents and the like. Microbiota found in and on humans are most preferred. Such microbiota are referred to herein as "mammalian microbiota" or "human microbiota" (wherein the term mammalian/human refers specifically to the localization/residence of the microbiota). Preferably, the tumor-related antigenic epitope is of the same species, in/on which the microbiota (of the microbiota sequence variant) reside. Preferably, the microbiota sequence variant is a human microbiota sequence variant. Accordingly, it is preferred that the tumor-related antigen is a human tumor-related antigen.

In general, the term "sequence variant", as used herein, i.e. throughout the present application, refers to a sequence which is similar (meaning in particular at least 50% sequence identity, see below), but not (100%) identical, to a reference sequence. Accordingly, a sequence variant contains at least one alteration in comparison to a reference sequence. Namely, the "microbiota sequence variant" is similar, but contains at least one alteration, in comparison to its reference sequence, which is a "tumor-related antigenic epitope sequence". Accordingly, it is also referred to the microbiota sequence variant as "microbiota sequence variant of a tumor-related antigenic epitope sequence". In other words, the "microbiota sequence variant" is a microbiota sequence (sequence of microbiota origin), which is a sequence variant of a tumor-related antigenic epitope sequence. That is, the "microbiota sequence variant" is a microbiota sequence (sequence of microbiota origin) is similar, but contains at least one alteration, in comparison to a tumor-related antigenic epitope sequence. Accordingly, the "microbiota sequence variant" is a microbiota sequence (and not a sequence variant of a microbiota sequence, which is no microbiota sequence). In general, a sequence variant (namely, a microbiota sequence) shares, in particular over the whole length of the sequence, at least 50% sequence identity with a reference sequence (the tumor-related antigenic epitope sequence), whereby sequence identity can be calculated as described below. Preferably, a sequence variant shares, in particular over the whole length of the sequence, at least 60%, preferably at least 70%, more preferably at least 75%, more preferably at least 80%, even more preferably at least 85%, still more preferably at least 90%, particularly preferably at least 95%, and most preferably at least 99% sequence identity with a reference sequence. Accordingly, it is preferred that the microbiota sequence variant shares at least 60%, preferably at least 70%, more preferably at least 75%, more preferably at least 80%, even more preferably at least 85%, still more preferably at least 90%, particularly preferably at least 95%, and most preferably at least 99% sequence identity with the tumor-related antigenic epitope sequence.

Preferably, a sequence variant preserves the specific function of the reference sequence. In the context of the present invention, this function is the functionality as an "epitope", i.e. it can be recognized by the immune system, in particular by antibodies, T cell receptors, and/or B cell receptors and, preferably, it can elicit an immune response.

The term "sequence variant" includes nucleotide sequence variants and amino acid sequence variants. For example, an amino acid sequence variant has an altered sequence in which one or more of the amino acids is deleted or substituted in comparison to the reference sequence, or one or more amino acids are inserted in comparison to the reference amino acid sequence. As a result of the alterations, the amino acid sequence variant has an amino acid sequence which is at least 50%, preferably at least 60%, more preferably at least 70%, more preferably at least 75%, even more preferably at least 80%, even more preferably at least 85%, still more preferably at least 90%, particularly preferably at least 95%, most preferably at least 99% identical to the reference sequence. For example, variant sequences which are at least 90% identical have no more than 10 alterations (i.e. any combination of deletions, insertions or substitutions) per 100 amino acids of the reference sequence.

In the context of the present invention, an amino acid sequence "sharing a sequence identity" of at least, for example, 95% to a query amino acid sequence of the present invention, is intended to mean that the sequence of the subject amino acid sequence is identical to the query sequence except that the subject amino acid sequence may include up to five amino acid alterations per each 100 amino acids of the query amino acid sequence. In other words, to obtain an amino acid sequence having a sequence of at least 95% identity to a query amino acid sequence, up to 5% (5 of 100) of the amino acid residues in the subject sequence may be inserted or substituted with another amino acid or deleted, preferably within the above definitions of variants or fragments. The same, of course, also applies similarly to nucleic acid sequences.

For (amino acid or nucleic acid) sequences without exact correspondence, a "% identity" of a first sequence (e.g., the sequence variant) may be determined with respect to a second sequence (e.g., the reference sequence). In general, the two sequences to be compared may be aligned to give a maximum correlation between the sequences. This may include inserting "gaps" in either one or both sequences, to enhance the degree of alignment. A % identity may then be determined over the whole length of each of the sequences being compared (so-called "global alignment"), that is particularly suitable for sequences of the same or similar length, or over shorter, defined lengths (so-called "local alignment"), that is more suitable for sequences of unequal length.

Methods for comparing the identity (sometimes also referred to as "similarity" or "homology") of two or more sequences are well known in the art. The percentage to which two (or more) sequences are identical can e.g. be determined using a mathematical algorithm. A preferred, but not limiting, example of a mathematical algorithm which can be used is the algorithm of Karlin et al. (1993), PNAS USA, 90:5873-5877. Such an algorithm is integrated in the BLAST family of programs, e.g. BLAST or NBLAST program (see also Altschul et al., 1990, J. Mol. Biol. 215, 405-410 or Altschul et al. (1997), Nucleic Acids Res, 25:3389-3402), accessible through the home page of the NCBI at world wide web site ncbi.nlm.nih.gov) and FASTA (Pearson (1990), Methods Enzymol. 183, 63-98; Pearson and Lipman (1988), Proc. Natl. Acad. Sci. U.S.A 85, 2444-2448). Sequences which are identical to other sequences to a certain extent can be identified by these programmes. Furthermore, programs available in the Wisconsin Sequence Analysis Package, version 9.1 (Devereux et al., 1984, Nucleic Acids Res., 387-395), for example the programs BESTFIT and GAP, may be used to determine the % identity between two polynucleotides and the % identity and the % homology or identity between two polypeptide sequences. BESTFIT uses the "local homology" algorithm of (Smith and Waterman (1981), J. Mol. Biol. 147, 195-197.) and finds the best single region of similarity between two sequences.

Preferably, the microbiota sequence variant differs from the tumor-related antigenic epitope sequence (only) in primary and/or secondary anchor residues for MHC molecules. More preferably, the microbiota sequence variant differs from the tumor-related antigenic epitope sequence (only) in that it comprises amino acid substitutions (only) in primary and/or secondary anchor residues for MHC molecules. Anchor residues for the HLA subtypes are known in the art, and were defined by large throughput analysis of structural data of existing p-HLA complexes in the Protein Data Bank. Moreover, anchor motifs for MHC subtypes can also be found in IEDB (URL: www.iedb.org; browse by allele) or in SYFPEITHI (URL: http://www.syfpeithi.de/). For example, for a 9 amino acid size HLA.A2.01 peptide, the peptide primary anchor residues, providing the main contact points, are located at residue positions P1, P2 and P9.

Accordingly, it is preferred that the core sequence of the microbiota sequence variant is identical with the core sequence of the tumor-related antigenic epitope sequence, wherein the core sequence consists of all amino acids except the three most N-terminal and the three most C-terminal amino acids. In other words, any alterations in the microbiota sequence variant in comparison to the tumor-related antigenic epitope sequence are preferably located within the three N-terminal and/or within the three C-terminal amino acids, but not in the "core sequence" (amino acids in the middle of the sequence). This does not mean that all three N-terminal and/or C-terminal amino acids must be altered, but only that those are the only amino acid position, where an amino acid can be altered. For example, in a peptide of nine amino acids, the three middle amino acids may represent the core sequence and alterations may preferably only occur at any of the three N-terminal and the three C-terminal amino acid positions.

More preferably, the core sequence consists of all amino acids except the two most N-terminal and the two most C-terminal amino acids. For example, in a peptide of nine amino acids, the five middle amino acids may represent the core sequence and alterations may preferably only occur at any of the two N-terminal and the two C-terminal amino acid positions.

It is also preferred that the core sequence consists of all amino acids except the most N-terminal and the most C-terminal amino acid. For example, in a peptide of nine amino acids, the seven middle amino acids may represent the core sequence and alterations may preferably only occur at the N-terminal position (P1) and the C-terminal amino acid position (P9).

Most preferably, the core sequence consists of all amino acids except the two most N-terminal amino acids and the most C-terminal amino acid. For example, in a peptide of nine amino acids, the six middle amino acids may represent the core sequence and alterations may preferably only occur at any of the two N-terminal positions (P1 and P2) and the C-terminal amino acid position (P9).

It is particularly preferred that the microbiota sequence variant, e.g. having a length of nine amino acids, comprises at position 1 (P1; the most N-terminal amino acid position) a phenylalanine (F) or a lysine (K). Moreover, it is preferred that the microbiota sequence variant, e.g. having a length of nine amino acids, comprises at position 2 (P2) a leucine (L) or a methionine (M). Moreover, it is preferred that the microbiota sequence variant, e.g. having a length of nine amino acids, comprises at position 9 (P9) a valine (V) or a leucine (L). Most preferably, the microbiota sequence variant, e.g. having a length of nine amino acids, comprises at position 1 (P1; the most N-terminal amino acid position) a phenylalanine (F) or a lysine (K), at position 2 (P2) a leucine (L) or a methionine (M) and/or at position 9 (P9) a valine (V) or a leucine (L).

Moreover, amino acid substitutions, in particular at positions other than the anchor position(s) for MHC molecules (e.g., P1, P2 and P9 for MHC-I subtype HLA.A2.01), are preferably conservative amino acid substitutions. Examples of conservative substitutions include substitution of one aliphatic residue for another, such as Ile, Val, Leu, or Ala for one another; or substitutions of one polar residue for another, such as between Lys and Arg; Glu and Asp; or Gln and Asn. Other such conservative substitutions, for example, substitutions of entire regions having similar hydrophobicity properties, are well known (Kyte and Doolittle, 1982, J. Mol. Biol. 157(1):105-132). Examples of conservative amino acid substitutions are presented in Table 1 below:

TABLE 1

| Original residues | Examples of substitutions |
|---|---|
| Ala (A) | Val, Leu, Ile, Gly |
| Arg (R) | His, Lys |
| Asn (N) | Gln |
| Asp (D) | Glu |
| Cys (C) | Ser |
| Gln (Q) | Asn |
| Glu (E) | Asp |
| Gly (G) | Pro, Ala |
| His (H) | Lys, Arg |
| Ile (I) | Leu, Val, Met, Ala, Phe |
| Leu (L) | Ile, Val, Met, Ala, Phe |
| Lys (K) | Arg, His |
| Met (M) | Leu, Ile, Phe |
| Phe (F) | Leu, Val, Ile, Tyr, Trp, Met |
| Pro (P) | Ala, Gly |
| Ser (S) | Thr |
| Thr (T) | Ser |
| Trp (W) | Tyr, Phe |
| Tyr (Y) | Trp, Phe |
| Val (V) | Ile, Met, Leu, Phe, Ala |

In particular, the above description of a (microbiota) sequence variant and its preferred embodiments, is applied in step (iii) of the method according to the present invention, wherein a microbiota sequence variant of a selected tumor-related antigenic epitope is identified. Accordingly, the identification in step (iii) of the method according to the present invention is in particular based on the principles outlined above for microbiota sequence variants.

In step (i) of the method for identification of a microbiota sequence variant of a tumor-related antigenic epitope sequence according to the present invention a tumor-related antigen of interest is selected. This may be done, for example, on basis of the cancer to be prevented and/or treated.

Antigens relating to distinct types of cancer are well-known in the art. Suitable cancer/tumor epitopes can be retrieved, for example, from cancer/tumor epitope databases, e.g. from the database "Tantigen" (TANTIGEN version 1.0, Dec. 1, 2009; developed by Bioinformatics Core at Cancer Vaccine Center, Dana-Farber Cancer Institute; URL: http://cvc.dfci.harvard.edu/tadb/). Further examples for databases of tumor-related antigens, which can be used in step (i) for selection include "Peptide Database" (https://www.cancerresearch.org/scientists/events-and-resources/peptide-database) and "CTdatabase" (http://www.cta.1-ncc.br/). In addition, the tumor-related antigen may also be selected based on literature, such as scientific articles, known in the art.

It is particularly preferred to combine internet resources providing databases of antigens (as exemplified above) with literature search. For example, in a sub-step (i-a) of step (i), one or more tumor-related antigens may be identified from a database, such as Tantigen, Peptide Database and/or CTdatabase, and in a sub-step (i-b) specific literature on the one or more antigens selected in sub-step (i-a) from a database may be identified and studied. Such literature may specifically relate to the investigation of specific tumor expression of antigens, such as Xu et al., An integrated genome-wide approach to discover tumor-specific antigens as potential immunologic and clinical targets in cancer. Cancer Res. 2012 Dec. 15; 72(24):6351-61; Cheevers et al., The prioritization of cancer antigens: a national cancer institute pilot project for the acceleration of translational research. Clin Cancer Res. 2009 Sep. 1; 15(17):5323-37.

Thereafter, a further round of selection may be performed in a sub-step (i-c), wherein the one or more antigen selected in sub-step (i-a) from a database may be selected (i.e. maintained) or "discarded" based on the result of the literature study in sub-step (i-b).

Optionally, the selected antigens may be annotated regarding the expression profile after selection (e.g., after sub-step (i-a) or (i-c), if those sub-steps are performed). To this end, tools such as Gent (http://medicalgenome.kribb.re.kr/GENT/), metabolic gene visualizer (http://merav.wi.mit.edu/), or protein Atlas (https://www.proteinatlas.org/) may be used. Thereby, the one or more selected antigen may be further defined, e.g. regarding the potential indication, its relation to possible side effects and/or whether it is a "driver" antigen (cancer-causative alteration) or a "passenger" antigen (incidental changes or changes occurring as a consequence of cancer) (see, for example, Tang J, Li Y, Lyon K, et al. Cancer driver-passenger distinction via sporadic human and dog cancer comparison: a proof of principle study with colorectal cancer. Oncogene. 2014; 33(7):814-822).

Preferably, the tumor-related antigenic epitope identified in step (ii) can be presented by MHC class I. In other words, it is preferred that, the tumor-related antigenic epitope identified in step (ii) can bind to MHC class I. MHC class I (major histocompatibility complex class I, MHC-I) presents epitopes to killer T cells, also called cytotoxic T lymphocytes (CTLs). A CTL expresses CDs receptors, in addition to TCRs (T-cell receptors). When a CTL's CDs receptor docks to a MHC class I molecule, if the CTL's TCR fits the epitope within the MHC class I molecule, the CTL triggers the cell to undergo programmed cell death by apoptosis. This route is particularly useful in prevention and/or treatment of cancer, since cancer cells are directly attacked. In humans, MHC class I comprises HLA-A, HLA-B, and HLA-C molecules.

Typically, peptides (epitopes) having a length of 8-12, preferably 8-10, amino acids are presented by MHC I. Which epitopes of an antigen can be presented by/bind to MHC I can be identified by the databases exemplified above (for example, Tantigen (TANTIGEN version 1.0, Dec. 1, 2009; developed by Bioinformatics Core at Cancer Vaccine Center, Dana-Farber Cancer Institute; URL: http://cvc.dfci.harvard.edu/tadb/) provides lists of epitopes with corresponding HLA sub-types). A preferred analysis tool is "IEDB" (Immune Epitope Database and Analysis Resource, IEDB Analysis Resource v2.17, supported by a contract from the National Institute of Allergy and Infectious Diseases, a component of the National Institutes of Health in the Department of Health and Human Services; URL: http://www.iedb.org/), which provides, for example, MHC-I processing predictions (http://tools.immuneepitope.org/analyze/html/mhceprocessing.html). Thereby, information regarding proteasomal cleavage, TAP transport, and MHC class I analysis tools can be combined for prediction of peptide presentation. Another preferred database is the major histocompatibility complex (MHC) databank "SYFPEITHI: a database of MHC ligands and peptide motifs (Ver. 1.0, supported by DFG-Sonderforschungsbereich 685 and the European Union: EU BIOMED CT95-1627, BIOTECH CT95-0263, and EU QLQ-CT-1999-00713; URL: www.syfpeithi.de), which compiles peptides eluted from MHC molecules. Since the SYFPEITHI database comprises only peptide sequences known to bind class I and class II MHC molecules from published reports, the SYFPEITHI database is preferred. Particularly preferably, the results obtained from in vitro data (such as those compiled in the SYFPEITHI database and IEDB database) may be extended by a restrictive search, for example including human linear epitopes obtained from elution assays and with MHC class I restriction, in an in silico prediction MHC binding database, e.g. IEDB database.

Additionally or alternatively to the above described database selection of epitopes presented by/binding to MHC I, binding of candidate peptides to MHC class I may be preferably tested by MHC in vitro or in silico binding tests. This also applies in general: binding of a peptide, such as an epitope or a microbiota sequence variant, may be preferably tested by the MHC in vitro or in silico binding tests as described herein.

In this context, for determination of binding to MHC class I the thresholds (cut-offs) provided by the IEDB Solutions Center (URL: https://help.iedb.org/hc/en-us/articles/114094151811-Selecting-thresholds-cut-offs-for-MHC-class-I-and-II-binding-predictions) may be used. Namely, for MHC class I the cutoffs shown in https://help.iedb.org/hc/en-us/articles/114094151811-Selecting-thresholds-cut-offs-for-MHC-class-I-and-II-binding-predictions and outlined in Table 2 may be used:

TABLE 2

Cutoffs for MHC class I binding predictions:

| Allele | Population frequency of allele | Allele specific affinity cutoff ($IC_{50}$ nM) |
|---|---|---|
| A*0101 | 16.2 | 884 |
| A*0201 | 25.2 | 255 |
| A*0203 | 3.3 | 92 |
| A*0206 | 4.9 | 60 |
| A*0301 | 15.4 | 602 |
| A*1101 | 12.9 | 382 |
| A*2301 | 6.4 | 740 |
| A*2402 | 16.8 | 849 |
| A*2501 | 2.5 | 795 |
| A*2601 | 4.7 | 815 |
| A*2902 | 2.9 | 641 |
| A*3001 | 5.1 | 109 |
| A*3002 | 5 | 674 |
| A*3101 | 4.7 | 329 |
| A*3201 | 5.7 | 131 |
| A*3301 | 3.2 | 606 |
| A*6801 | 4.6 | 197 |
| A*6802 | 3.3 | 259 |
| B*0702 | 13.3 | 687 |
| B*0801 | 11.5 | 663 |
| B*1402 | 2.8 | 700 |
| B*1501 | 5.2 | 528 |
| B*1801 | 4.4 | 732 |
| B*2705 | 2 | 584 |
| B*3501 | 6.5 | 348 |
| B*3503 | 1.2 | 888 |
| B*3801 | 2 | 944 |
| B*3901 | 2.9 | 542 |
| B*4001 | 10.3 | 639 |
| B*4002 | 3.5 | 590 |
| B*4402 | 9.2 | 904 |

TABLE 2-continued

Cutoffs for MHC class I binding predictions:

| Allele | Population frequency of allele | Allele specific affinity cutoff (IC$_{50}$ nM) |
|---|---|---|
| B*4403 | 7.6 | 780 |
| B*4601 | 4 | 926 |
| B*4801 | 1.8 | 887 |
| B*5101 | 5.5 | 939 |
| B*5301 | 5.4 | 538 |
| B*5701 | 3.2 | 716 |

(derived from URL: https://help.iedb.org/hc/en-us/articles/114094151811-Selecting-thresholds-cut-offs-for-MHC-class-I-and-II-binding-predictions)

Prediction of MHC class I binding (MHC in silico binding test) may be performed using publicly available tools, such as "NetMHCpan 3.0 Server" (Center for biological sequence analysis, Technical University of Denmark DTU; URL: http://www.cbs.dtu.dk/services/NetMHCpan/). The NetMHCpan 3.0 method is trained on more than 180000 quantitative binding data covering 172 MHC molecules from human (HLA-A, B, C, E) and other species. The affinity may be predicted by leaving default thresholds for strong and weak binders. For example, for HLA-A*0201 a calculated affinity below 50 nM may be indicate "strong binders", and between 50 and 255 nM (or 50 nM and 300 nM) may indicate "moderate binders".

In NetMHCpan 3.0, the rank of the predicted affinity may be compared to a set of 400000 random natural peptides, which may be used as a measure of the % rank binding affinity. This value is not affected by inherent bias of certain molecules towards higher or lower mean predicted affinities. For example (e.g., for HLA-A*0201), very strong binders may be defined as having % rank <0.5, strong binders may be defined as having % rank <1.0, moderate binders may be defined as having % rank from 1.0 to 2.0, and weak binders may be defined as having a % rank >2.0.

A method for in vitro testing is well-known to the skilled person. For example, the skilled person may use the experimental protocol as validated for peptides presented by HLA-A*0201 in Tourdot et al., A general strategy to enhance immunogenicity of low-affinity HLA-A2.1-associated peptides: implication in the identification of cryptic tumor epitopes. Eur J Immunol. 2000 December; 30(12): 3411-21. In this context, a reference peptide, such as HIV pol 589-597, may be additionally used in the test. This enables calculation of the in vitro affinity relative to the binding observed with the reference peptide, e.g. by the following equation:

Relative affinity=concentration of each peptide inducing 20% of expression of HLA-A*0201/ concentration of the reference peptide inducing 20% of expression of HLA-A*0201

(where 100% is the level of HLA-A*0201 expression detected with the reference peptide, e.g. HIV pol 589-597, for example used at a 100 μM concentration). For example, a peptide displaying a relative affinity below 1 may be considered as a "strong binder", a peptide displaying relative affinity between 1 and 2 may be considered as a "moderate binder" and a peptide displaying relative affinity more than s may be considered as a "weak binder".

It is also preferred that the tumor-related antigenic epitope identified in step (ii) can be presented by MHC class II. In other words, it is preferred that, the tumor-related antigenic epitope identified in step (ii) can bind to MHC class II. MHC class II (major histocompatibility complex class II, MHC-II) presents epitopes to immune cells, like the T helper cell (CD4+ T-cells). Then, the helper T cells help to trigger an appropriate immune response which may lead to a full-force antibody immune response due to activation of B cells. In humans, MHC class II comprises HLA-DP, HLA-DM, HLA-DOA, HLA-DOB, HLA-DQ and HLA-DR molecules.

Typically, peptides (epitopes) having a length of 13-24 amino acids are presented by MHC II. Which epitopes of an antigen can be presented by/bind to MHC II can be identified by the databases as outlined above for MHC I (only that the tools relating to MHC II may be used instead of MHC I). Additionally or alternatively, binding of candidate peptides to MHC class II may be preferably tested by MHC in vitro or in silico binding tests as described herein, which also apply to MHC II in a similar manner.

Identification of at least one microbiota sequence variant of the epitope sequence in step (iii) of the method for identification of a microbiota sequence variant according to the present invention is preferably done by:
  comparing the epitope sequence selected in step (ii) to one or more microbiota sequence(s), and
  identifying whether the one or more microbiota sequence(s) contain one or more microbiota sequence variant(s) of the epitope sequence (as outlined above).

In this context, the criteria (in particular regarding similarity and % sequence identity) for the microbiota sequence variant outlined above, and in particular the preferred embodiments of the microbiota sequence variant described above, are applied. For example, in a first step a sequence similarity search, such as BLAST or FASTA may be performed. For example, a protein BLAST (blastp) may be performed using the PAM30 protein substitution matrix. The PAM30 protein substitution matrix describes the rate of amino acid changes per site over time, and is recommended for queries with lengths under 35 amino acids. Further (additional) exemplified parameters of the protein BLAST may be a word size of 2 (suggested for short queries); an Expect value (E) of 20000000 (adjusted to maximize the number of possible matches); and/or the composition-based-statistics set to '0', being the input sequences shorter than so amino acids, and allowing only un-gapped alignments.

Thereafter, the results may be filtered, for example regarding the sequence length, for example such that only sequences having a length of 8-12 amino acids (e.g., only sequences having a length of 8 amino acids, only sequences having a length of 9 amino acids, only sequences having a length of 10 amino acids, only sequences having a length of 11 amino acids, or only sequences having a length of 12 amino acids), preferably only sequences having a length of 8-10 amino acids, most preferably only sequences having a length of 9 amino acids, are obtained.

Furthermore, the results may (additionally) be filtered such that mismatches/substitutions are only allowed at certain positions, preferably only at the N- and/or C-terminus, but not in the core sequence as described above. As a specific example the results may be filtered such that only sequences having a length of 9 amino acids with mismatches/substitutions only allowed at positions P1, P2 and P9 and with a maximum of two mismatches allowed per sequence, may be obtained.

The one or more microbiota sequence(s), to which the epitope sequence is compared to, may be any microbiota sequence or any compilation of microbiota sequences (such as any microbiota sequence database).

Preferably, the microbiota sequence variant in step (iii) is identified on basis of a microbiota (sequence) database. Such databases may preferably comprise microbiota (sequence) data of multiple individuals (subjects). An example of such a database is the "Integrated reference catalog of the human gut microbiome" (version 1.0, March 2014; Li et al. MetaHIT Consortium. An integrated catalog of reference genes in the human gut microbiome. Nat Biotechnol. 2014 August; 52(8):834-41; URL: http://meta.genomics.cn/meta/home), which includes data from the major human microbiome profiling efforts, the American National Institutes of Health Human Microbiome Project (NIH-HMP) and the European Metagenomics of the Human Intestinal Tract Initiative (MetaHIT).

It is also preferred that the microbiota database comprises microbiota data of a single individual, but not of multiple individuals. In this way, the microbiota sequence variant (or a medicament comprising the same) can be specifically tailored for an individual. In addition to the advantage that the microbiota sequence variants (identified by a method) of the present invention are distinct from self-antigens, thereby avoiding self-tolerance of the immune system, a microbiota sequence variant present in an individual has the additional advantage that the individual may be "primed" for such a microbiota sequence variant, i.e. the individual may have memory T-cells primed by the microbiota sequence variant. In particular, existing memory T-cells against the microbiota sequence variant of a human tumor-related antigenic epitope will be reactivated with a challenge of the microbiota sequence variant and will strengthened and accelerate establishment of an anti-tumoral response, thereby further increasing therapeutic efficacy.

A database comprising microbiota data of a single individual, but not of multiple individuals, may be compiled, for example, by the use of one or more stool samples of the individual. For example, microbial (in particular bacterial) nucleic acids (such as DNA) or (poly)peptides may be extracted from the stool sample and sequenced by methods known in the art. The sequences may then be compiled in a database containing only microbiota data, in particular sequences. In a particularly preferred example, the sequencing of the DNA extracted from a stool sample can be performed, e.g. at 40 million pair end reads for example on an Illumina HiSeq. Sequences can be analyzed, for example, using bioinformatics pipeline for identification of genomic part of candidate bacteria expressing the microbiota sequence variant (e.g., a bacterial peptide).

Preferably, step (iii) of the method for identification of a microbiota sequence variant according to the present invention comprises the following sub-steps:
   (iii-a) optionally, identifying microbiota protein sequences or nucleic acid sequences from (a) sample(s) of a single or multiple individual(s),
   (iii-b) compiling a database containing microbiota protein sequences or nucleic acid sequences of a single or multiple individual(s), and
   (iii-c) identifying in the database compiled in step (iii-b) at least one microbiota sequence variant of the epitope sequence identified in step (ii).

The sample in step (iii-a) is preferably a stool sample. Depending on whether the database to be compiled shall relate to a single or multiple individuals, one or more stool samples of a single or multiple individuals may be used.

The identification step (iii-a) preferably comprises extraction of microbial (in particular bacterial) nucleic acids (such as DNA) or (poly)peptides from the sample, in particular the stool sample and sequencing thereof, e.g. as described above. Optionally, sequences may be analyzed as described above.

Preferably, the method according to the present invention further comprises the following step:

(iv) testing binding of the at least one microbiota sequence variant to MHC molecules, in particular MHC I molecules, and obtaining a binding affinity.

Binding of the at least one microbiota sequence variant to MHC molecules, in particular to MHC I or MHC II, may be tested by the MHC in vitro or in silico binding tests as described above. Accordingly, moderate, strong and very strong binders may be selected as described above.

Preferably, binding to MHC is tested (in vitro and/or in silico as described herein) for the at least one microbiota sequence variant to MHC molecules and, additionally, for the (respective reference) epitope to MHC molecules, in particular MHC I or MHC II molecules, and binding affinities are preferably obtained for both (the epitope sequence and the microbiota sequence variant thereof).

After the binding test, preferably only such microbiota sequence variants are selected, which bind moderately, strongly or very strongly to MHC, in particular MHC I or MHC II. More preferably only strong and very strong binders are selected and most preferably, only such microbiota sequence variants are selected, which bind very strongly to MHC, in particular MHC I or MHC II.

More preferably, only such microbiota sequence variants are selected, which bind strongly or very strongly to MHC, in particular MHC I or MHC II, and wherein the (respective reference) epitope binds moderately, strongly or very strongly to MHC, in particular MHC I or MHC II. Even more preferably, only such microbiota sequence variants are selected, which bind very strongly to MHC, in particular MHC I or MHC II, and wherein the (respective reference) epitope binds moderately, strongly or very strongly to MHC, in particular MHC I or MHC II. Most preferably, only such microbiota sequence variants are selected, which bind very strongly to MHC, in particular MHC I or MHC II, and wherein the (respective reference) epitope binds strongly or very strongly to MHC, in particular MHC I or MHC II.

It is also preferred that the step (iv) of the method according to the present invention further comprises a comparison of the binding affinities obtained for the microbiota sequence variant and for the respective reference epitope and selecting microbiota sequence variants having a higher binding affinity to MHC, in particular MHC I or MHC II, than their respective reference epitopes.

Preferably, the method according to the present invention further comprises the following step:

(v) determining cellular localization of a microbiota protein containing the microbiota sequence variant.

In this context, it is preferably determined whether the microbiota protein containing the microbiota sequence variant (i) is secreted and/or (ii) comprises a transmembrane domain. Microbiota proteins, which are secreted or present in/on the membrane may elicit an immune response. Therefore, in the context of the present invention microbiota sequence variants, which are comprised in a microbiota protein, which is secreted (e.g., comprise a signal peptide) or which comprises a transmembrane domain, are preferred. In particular, microbiota sequence variants comprised in secreted proteins (or proteins having a signal peptide) are preferred, since secreted components or proteins contained in secreted exosomes are more prone to be presented by APCs.

In order to determine cellular localization of the microbiota protein containing the microbiota sequence variant step (v) preferably further comprises identifying the sequence of a microbiota protein containing the microbiota sequence variant, preferably before determining cellular localization.

Cellular localization, in particular whether a protein is secreted or comprises a transmembrane domain, can be tested in silico or in vitro by methods well-known to the skilled person. For example "SignalP 4.1 Server" (Center for biological sequence analysis, Technical University of Denmark DTU; URL: www.cbs.dtu.dk/services/SignalP) and/or "Phobius" (A combined transmembrane topology and signal peptide predictor, Stockholm Bioinformatics Centre; URL: phobius.sbc.su.se) may be used. Preferably, two prediction tools (e.g., SignalP 4.1 Server and Phobius) may be combined.

For example, to test whether a protein is secreted, presence of a signal peptide may be assessed. Signal peptides are ubiquitous protein-sorting signals that target their passenger (cargo) protein for translocation across the cytoplasmic membrane in prokaryotes. To test presence of a signal peptide, for example "SignalP 4.1 Server" (Center for biological sequence analysis, Technical University of Denmark DTU; URL: www.cbs.dtu.dk/services/SignalP) and/or "Phobius" (A combined transmembrane topology and signal peptide predictor, Stockholm Bioinformatics Centre; URL: phobius.sbc.su.se) may be used. Preferably, two prediction tools (e.g., SignalP 4.1 Server and Phobius) may be combined.

Moreover, it may be determined whether a protein comprises a transmembrane domain. Both, signal peptides and transmembrane domains are hydrophobic, but transmembrane helices typically have longer hydrophobic regions. For example, SignalP 4.1 Server and Phobius have the capacity to differentiate signal peptides from transmembrane domains. Preferably, a minimum number of two predicted transmembrane helices is set to differentiate between membrane and cytoplasmic proteins to deliver the final consensus list.

Preferably, the method according to the present invention comprises step (iv) as described above and step (v) as described above. Preferably, step (v) follows step (iv). It is also preferred that step (iv) follows step (v).

Moreover, it is also preferred that the method according to the present invention comprises the following step:
annotation of the microbiota protein comprising the microbiota sequence variant.

Annotation may be performed by a (BLAST-based) comparison against reference database, for example against the Kyoto Encyclopedia of Genes and Genomes (KEGG) and/or against the National Center for Biotechnology Information (NCBI) Reference Sequence Database (RefSeq). RefSeq provides an integrated, non-redundant set of sequences, including genomic DNA, transcripts, and proteins. In KEGG, the molecular-level functions stored in the KO (KEGG Orthology) database may be used. These functions are categorized in groups of orthologs, which contain proteins encoded by genes from different species that evolved from a common ancestor.

Method for Preparing a Medicament

In a further aspect the present invention provides a method for preparing a medicament, preferably for prevention and/or treatment of cancer, comprising the following steps:
(a) identification of a microbiota sequence variant of a tumor-related antigenic epitope sequence according to the method according the present invention as described above; and
(b) preparing a medicament comprising the microbiota sequence variant (i.e., peptide or nucleic acid).

Preferably, the medicament is a vaccine. As used in the context of the present invention, the term "vaccine" refers to a biological preparation that provides innate and/or adaptive immunity, typically to a particular disease, preferably cancer. Thus, a vaccine supports in particular an innate and/or an adaptive immune response of the immune system of a subject to be treated. For example, the microbiota sequence variant as described herein typically leads to or supports an adaptive immune response in a patient to be treated. The vaccine may further comprise an adjuvant, which may lead to or support an innate immune response.

Preferably, the preparation of the medicament, i.e. step (b) of the method for preparing a medicament according to the present invention, comprises loading a nanoparticle with the microbiota sequence variant or with a polypeptide/protein comprising the microbiota sequence variant (or a nucleic acid molecule comprising the microbiota sequence variant), wherein the microbiota sequence variant is preferably a peptide as described above. In particular, the nanoparticle is used for delivery of the microbiota sequence variant (the polypeptide/protein/nucleic acid comprising the microbiota sequence variant) and may optionally also act as an adjuvant. The microbiota sequence variant (the polypeptide/protein/nucleic acid comprising the microbiota sequence variant) is typically either encapsulated within the nanoparticle or bound to (decorated onto) the surface of the nanoparticle ("coating").

Nanoparticles, in particular for use as vaccines, are known in the art and described, for example, in Shao K, Singha S, Clemente-Casares X, Tsai S, Yang Y, Santamaria P (2015): Nanoparticle-based immunotherapy for cancer, ACS Nano 9(1):16-50; Zhao L, Seth A, Wibowo N, Zhao C X, Mitter N, Yu C, Middelberg A P (2014): Nanoparticle vaccines, Vaccine 32(3):327-37; and Gregory A E, Titball R, Williamson D (2013) Vaccine delivery using nanoparticles, Front Cell Infect Microbiol. 3:13, doi: 10.3389/fcimb.2013.00013. eCollection 2013, Review. Compared to conventional approaches, nanoparticles can protect the payload (antigen/adjuvant) from the surrounding biological milieu, increase its half-life, minimize its systemic toxicity, promote its delivery to APCs, or even directly trigger the activation of TAA-specific T-cells. Preferably, the nanoparticle has a size (diameter) of no more than 300 nm, more preferably of no more than 200 nm and most preferably of no more than 100 nm. Such nanoparticles are adequately sheltered from phagocyte uptake, with high structural integrity in the circulation and long circulation times, capable of accumulating at sites of tumor growth, and able to penetrate deep into the tumor mass.

Examples of nanoparticles include polymeric nanoparticles, such as poly(ethylene glycol) (PEG) and poly (D,L-lactic-coglycolic acid) (PLGA); inorganic nanoparticles, such as gold nanoparticles, iron oxide beads, iron-oxide zinc-oxide nanoparticles, carbon nanotubes and mesoporous silica nanoparticles; liposomes, such as cationic liposomes; immunostimulating complexes (ISCOM); virus-like particles (VLP); and self-assembled proteins.

Polymeric nanoparticles are nanoparticles based on/comprising polymers, such as poly(d,l-lactide-co-glycolide) (PLG), poly(d,l-lactic-coglycolic acidxPLGA), poly(g-glutamic acid) (g-PGA), poly(ethylene glycol) (PEG), and polystyrene. Polymeric nanoparticles may entrap an antigen (e.g., the microbiota sequence variant or a (poly)peptide comprising the same) or bind to/conjugate to an antigen (e.g., the microbiota sequence variant or a (poly)peptide comprising the same). Polymeric nanoparticles may be used for delivery, e.g. to certain cells, or sustain antigen release by virtue of their slow biodegradation rate. For example, g-PGA nanoparticles may be used to encapsulate hydrophobic antigens. Polystyrene nanoparticles can conjugate to a variety of antigens as they can be surface-modified with various functional groups. Polymers, such as Poly(L-lactic acid) (PLA), PLGA, PEG, and natural polymers such as polysaccharides may also be used to synthesize hydrogel nanoparticles, which are a type of nano-sized hydrophilic three-dimensional polymer network. Nanogels have favorable properties including flexible mesh size, large surface area for multivalent conjugation, high water content, and high loading capacity for antigens. Accordingly, a preferred nanoparticle is a nanogel, such as a chitosan nanogel. Preferred polymeric nanoparticles are nanoparticles based on/comprising poly(ethylene glycol) (PEG) and poly (D,L-lactic-coglycolic acid) (PLGA).

Inorganic nanoparticles are nanoparticles based on/comprising inorganic substances, and examples of such nanoparticles include gold nanoparticles, iron oxide beads, iron-oxide zinc-oxide nanoparticles, carbon nanoparticles (e.g., carbon nanotubes) and mesoporous silica nanoparticles. Inorganic nanoparticles provide a rigid structure and controllable synthesis. For example, gold nanoparticles can be easily produced in different shapes, such as spheres, rods, cubes. Inorganic nanoparticles may be surface-modified, e.g. with carbohydrates. Carbon nanoparticles provide good biocompatibility and may be produced, for example, as nanotubes or (mesoporous) spheres. For example, multiple copies of the microbiota sequence variant according to the present invention (or a (poly)peptide comprising the same) may be conjugated onto carbon nanoparticles, e.g. carbon nanotubes. Mesoporous carbon nanoparticles are preferred for oral administration. Silica-based nanoparticles (SiNPs) are also preferred. SiNPs are biocompatible and show excellent properties in selective tumor targeting and vaccine delivery. The abundant silanol groups on the surface of SiNPs may be used for further modification to introduce additional functionality, such as cell recognition, absorption of specific biomolecules, improvement of interaction with cells, and enhancement of cellular uptake. Mesoporous silica nanoparticles are particularly preferred.

Liposomes are typically formed by phospholipids, such as 1,2-dioleoyl-s-trimethylammonium propane (DOTAP). In general, cationic liposomes are preferred. Liposomes are self-assembling with a phospholipid bilayer shell and an aqueous core. Liposomes can be generated as unilameller vesicles (having a single phospholipid bilayer) or as multilameller vesicles (having several concentric phospholipid shells separated by layers of water). Accordingly, antigens can be encapsulated in the core or between different layers/shells. Preferred liposome systems are those approved for human use, such as Inflexal® V and Epaxal®.

Immunostimulating complexes (ISCOM) are cage like particles of about 40 nm (diameter), which are colloidal saponin containing micelles, for example made of the saponin adjuvant Quil A, cholesterol, phospholipids, and the (poly)peptide antigen (such as the microbiota sequence variant or a polypeptide comprising the same). These spherical particles can trap the antigen by apolar interactions. Two types of ISCOMs have been described, both of which consist of cholesterol, phospholipid (typically either phosphatidylethanolamine or phos-phatidylcholine) and saponin (such as QuilA).

Virus-like particles (VLP) are self-assembling nanoparticles formed by self-assembly of biocompatible capsid proteins. Due to the naturally-optimized nanoparticle size and repetitive structural order VLPs can induce potent immune responses. VLPs can be derived from a variety of viruses with sizes ranging from 20 nm to 800 nm, typically in the range of 20-150 nm. VLPs can be engineered to express additional peptides or proteins either by fusing these peptides/proteins to the particle or by expressing multiple antigens. Moreover, antigens can be chemically coupled onto the viral surface to produce bioconjugate VLPs.

Examples of self-assembled proteins include ferritin and major vault protein (MVP). Ferritin is a protein that can self-assemble into nearly-spherical 10 nm structure. Ninety-six units of MVP can self-assemble into a barrel-shaped vault nanoparticle, with a size of approximately 40 nm wide and 70 nm long. Antigens that are genetically fused with a minimal interaction domain can be packaged inside vault nanoparticles by self-assembling process when mixed with MVPs. Accordingly, the antigen (such as the microbiota sequence variant according to the present invention of a polypeptide comprising the same) may be fused to a self-assembling protein or to a fragment/domain thereof, such as the minimal interaction domain of MVP. Accordingly, the present invention also provides a fusion protein comprising a self-assembling protein (or a fragment/domain thereof) and the microbiota sequence variant according to the present invention.

In general, preferred examples of nanoparticles (NPs) include iron oxide beads, polystyrene microspheres, poly(y-glutamic acid) (y-PGA) NPs, iron oxide-zinc oxide NPs, cationized gelatin NPs, pluronic-stabilized poly(propylene sulfide) (PPS) NPs, PLGA NPs, (cationic) liposomes, (pH-responsive) polymeric micelles, PLGA, cancer cell membrane coated PLGA, lipid-calcium-phosphate (LCP) NPs, liposome-protamine-hyaluronic acid (LPH) NPs, polystyrene latex beads, magnetic beads, iron-dextran particles and quantum dot nanocrystals.

Preferably, step (b) further comprises loading the nanoparticle with an adjuvant, for example a toll-like receptor (TLR) agonist. Thereby, the microbiota sequence variant (the polypeptide/protein/nucleic acid comprising the microbiota sequence variant) can be delivered together with an adjuvant, for example to antigen-presenting cells (APCs), such as dendritic cells (DCs). The adjuvant may be encapsulated by the nanoparticle or bound to/conjugated to the surface of the nanoparticle, preferably similarly to the microbiota sequence variant.

It is also preferred that the preparation of the medicament, i.e. step (b) of the method for preparing a medicament according to the present invention, comprises loading a bacterial cell with the microbiota sequence variant. For example, the bacterial cell may comprise a nucleic acid molecule encoding the microbiota sequence variant and/or express the microbiota sequence variant (as peptide or comprised in a polypeptide/protein). To this end, step (b) preferably comprises a step of transformation of a bacterial cell with (a nucleic acid molecule comprising/encoding) the microbiota sequence variant (which is in this context preferably a nucleic acid). Such a bacterial cell may serve as "live bacterial vaccine vectors", wherein live bacterial cells (such as bacteria or bacterial spores, e.g., endospores, exospores or microbial cysts) can serve as vaccines. Preferred examples thereof are described in da Silva et al., J Microbiol. 2015 Mar. 4; 45(4):1117-29.

Bacterial cells (such as bacteria or bacterial spores, e.g., endospores, exospores or microbial cysts), in particular (entire) gut bacterial species, can be advantageous, as they have the potential to trigger a greater immune response than the (poly)peptides or nucleic acids they contain.

Preferably, the bacterial cell is a gut bacterial cell, i.e. a bacterial cell (of a bacterium) residing in the gut.

Alternatively, bacterial cells, in particular gut bacteria, according to the invention may be in the form of probiotics, i.e. of live gut bacterium, which can thus be used as food additive due to the health benefits it can provide. Those can be for example lyophilized in granules, pills or capsules, or directly mixed with dairy products for consumption.

Preferably, the preparation of the medicament, i.e. step (b) of the method for preparing a medicament according to the present invention, comprises the preparation of a pharmaceutical composition. Such a pharmaceutical composition preferably comprises (i) the microbiota sequence variant;
(ii) a (recombinant) protein comprising the microbiota sequence variant;
(iii) an (immunogenic) compound comprising the microbiota sequence variant;
(iv) a nanoparticle loaded with the microbiota sequence variant;
(v) an antigen-presenting cell loaded with the microbiota sequence variant;
(vi) a host cell, such as a bacterial cell, expressing the microbiota sequence variant; or
(vii) a nucleic acid molecule encoding the microbiota sequence variant;

and, optionally, a pharmaceutically acceptable carrier and/or an adjuvant.

Formulation processing techniques, which are useful in the context of the preparation of medicaments, in particular pharmaceutical compositions and vaccines, according to the present invention are set out in "Part 5 of Remington's "The Science and Practice of Pharmacy", $22^{nd}$ Edition, 2012, University of the Sciences in Philadelphia, Lippincott Williams & Wilkins".

A recombinant protein, as used herein, is a protein, which does not occur in nature, for example a fusion protein comprising the microbiota sequence variant and further components.

The term "immunogenic compound" refers to a compound comprising the microbiota sequence variant as defined herein, which is also able to induce, maintain or support an immunological response against the microbiota sequence variant in a subject to whom it is administered. In some embodiments, immunogenic compounds comprise at least one microbiota sequence variant, or alternatively at least one compound comprising such a microbiota sequence variant, linked to a protein, such as a carrier protein, or an adjuvant. A carrier protein is usually a protein, which is able to transport a cargo, such as the microbiota sequence variant. For example, the carrier protein may transport its cargo across a membrane.

As a further ingredient, the pharmaceutical composition may in particular comprise a pharmaceutically acceptable carrier and/or vehicle. In the context of the present invention, a pharmaceutically acceptable carrier typically includes the liquid or non-liquid basis of the inventive pharmaceutical composition. If the inventive pharmaceutical composition is provided in liquid form, the carrier will typically be pyrogen-free water; isotonic saline or buffered (aqueous) solutions, e.g phosphate, citrate etc. buffered solutions. Particularly for injection of the inventive inventive pharmaceutical composition, water or preferably a buffer, more preferably an aqueous buffer, may be used, containing a sodium salt, preferably at least so mM of a sodium salt, a calcium salt, preferably at least 0.05 mM of a calcium salt, and optionally a potassium salt, preferably at least 1 mM of a potassium salt. According to a preferred embodiment, the sodium, calcium and, optionally, potassium salts may occur in the form of their halogenides, e.g. chlorides, iodides, or bromides, in the form of their hydroxides, carbonates, hydrogen carbonates, or sulfates, etc. Without being limited thereto, examples of sodium salts include e.g. NaCl, NaI, NaBr, $Na_2CO_3$, $NaHCO_3$, $Na_2SO_4$, examples of the optional potassium salts include e.g. KCl, KI, KBr, $K_2CO_3$, $KHCO_3$, $K_2SO_4$, and examples of calcium salts include e.g. $CaCl_2$, CaI, $CaBr_2$, $CaCO_3$, $CaSO_4$, $Ca(OH)_2$. Furthermore, organic anions of the aforementioned cations may be contained in the buffer. According to a more preferred embodiment, the buffer suitable for injection purposes as defined above, may contain salts selected from sodium chloride (NaCl), calcium chloride ($CaCl_2$) and optionally potassium chloride (KCl), wherein further anions may be present additional to the chlorides. $CaCl_2$ can also be replaced by another salt like KCl. Typically, the salts in the injection buffer are present in a concentration of at least so mM sodium chloride (NaCl), at least 1 mM potassium chloride (KCl) and at least 0.05 mM calcium chloride ($CaCl_2$). The injection buffer may be hypertonic, isotonic or hypotonic with reference to the specific reference medium, i.e. the buffer may have a higher, identical or lower salt content with reference to the specific reference medium, wherein preferably such concentrations of the afore mentioned salts may be used, which do not lead to damage of cells due to osmosis or other concentration effects. Reference media are e.g. liquids occurring in "in vivo" methods, such as blood, lymph, cytosolic liquids, or other body liquids, or e.g. liquids, which may be used as reference media in "in vitro" methods, such as common buffers or liquids. Such common buffers or liquids are known to a skilled person. Saline (0.9% NaCl) and Ringer-Lactate solution are particularly preferred as a liquid basis.

Moreover, one or more compatible solid or liquid fillers or diluents or encapsulating compounds may be used as well for the inventive pharmaceutical composition, which are suitable for administration to a subject to be treated. The term "compatible" as used herein means that these constituents of the inventive pharmaceutical composition are capable of being mixed with the microbiota sequence variant as defined herein in such a manner that no interaction occurs which would substantially reduce the pharmaceutical effectiveness of the inventive pharmaceutical composition under typical use conditions. Pharmaceutically acceptable carriers, fillers and diluents must, of course, have sufficiently high purity and sufficiently low toxicity to make them suitable for administration to a subject to be treated. Some examples of compounds which can be used as pharmaceutically acceptable carriers, fillers or constituents thereof are sugars, such as, for example, lactose, glucose and sucrose; starches, such as, for example, corn starch or potato starch; cellulose and its derivatives, such as, for example, sodium carboxymethylcellulose, ethylcellulose, cellulose acetate; powdered tragacanth; malt; gelatin; tallow; solid glidants, such as, for example, stearic acid, magnesium stearate; calcium sulfate; vegetable oils, such as, for example, groundnut oil, cottonseed oil, sesame oil, olive oil, corn oil and oil from *theobroma*; polyols, such as, for example, polypropylene glycol, glycerol, sorbitol, mannitol and polyethylene glycol; alginic acid.

Preferably, the microbiota sequence variant as described herein, or a polypeptide comprising the microbiota sequence variant, may be co-administered or linked, for example by covalent or non-covalent bond, to a protein/peptide having immuno-adjuvant properties, such as providing stimulation of CD4+ Th1 cells. While the microbiota sequence variant as described herein preferably binds to MHC class I, CD4+ helper epitopes may be additionally used to provide an efficient immune response. Th1 helper cells are able to sustain efficient dendritic cell (DC) activation and specific CTL activation by secreting interferon-gamma (IFN-γ), tumor necrosis factor-alpha (TNF-α) and interleukine-2 (II-2) and enhancing expression of costimulatory signal on DCs and T cells (Galaine et al., Interest of Tumor-Specific CD+ T Helper 1 Cells for Therapeutic Anticancer Vaccine. Vaccines (Basel). 2015 Jun. 30; 3(3):490-502).

For example, the adjuvant peptide/protein may preferably be a non-tumor antigen that recalls immune memory or provides a non-specific help or could be a specific tumor-derived helper peptide. Several helper peptides have been described in the literature for providing a nonspecific T cell help, such as tetanus helper peptide, keyhole limpet hemocyanin peptide or PADRE peptide (Adotévi et al., Targeting antitumor CD4 helper T cells with universal tumor-reactive helper peptides derived from telomerase for cancer vaccine. Hum Vaccin Immunother. 2013 May; 9(5):1073-7, Slingluff. The present and future of peptide vaccines for cancer: single or multiple, long or short, alone or in combination? Cancer J. 2011 September-October; 17(5):54-50). Accordingly, tetanus helper peptide, keyhole limpet hemocyanin peptide and PADRE peptide are preferred examples of such adjuvant peptide/proteins. Moreover, specific tumor derived helper peptides are preferred. Specific tumor derived helper peptides are typically presented by MHC class II, in particular by HLA-DR, HLA-DP or HLA-DQ. Specific tumor derived helper peptides may be fragments of sequences of shared overexpressed tumor antigens, such as HER2, NY-ESO-1, hTERT or IL13RA2. Such fragments have preferably a length of at least 10 amino acids, more preferably of at least 11 amino acids, even more preferably of at least 12 amino acids and most preferably of at least is amino acids. In particular, fragments of shared overexpressed tumor antigens, such as HER2, NY-ESO-1, hTERT or IL13RA2, having a length of is to 24 amino acids are preferred. Preferred fragments bind to MHC class II and may, thus, be identified using, for example, the MHC class II binding prediction tools of IEDB (Immune epitope database and analysis resource; Supported by a contract from the National Institute of Allergy and Infectious Diseases, a component of the National Institutes of Health in the Department of Health and Human Services; URL: http://www.iedb.org/; http://tools.iedb.org/mhcii/).

Accordingly, the pharmaceutical composition, in particular the vaccine, can additionally contain one or more auxiliary substances in order to further increase its immunogenicity, preferably the adjuvants described above. A synergistic action of the microbiota sequence variant as defined above and of an auxiliary substance, which may be optionally contained in the inventive vaccine as described above, is preferably achieved thereby. Depending on the various types of auxiliary substances, various mechanisms can come into consideration in this respect. For example, compounds that permit the maturation of dendritic cells (DCs), for example lipopolysaccharides, TNF-alpha or CD40 ligand, form a first class of suitable auxiliary substances. In general, it is possible to use as auxiliary substance any agent that influences the immune system in the manner of a "danger signal" (LPS, GP96, etc.) or cytokines, such as GM-CSF, which allow an immune response produced by the immune-stimulating adjuvant according to the invention to be enhanced and/or influenced in a targeted manner. Particularly preferred auxiliary substances are cytokines, such as monokines, lymphokines, interleukins or chemokines, that further promote the innate immune response, such as IL-1, IL-2, IL-3, IL-4, IL-5, II-6, IL-7, IL-8, IL-9, IL-10, IL-12, IL-13, IL-14, IL-15, IL-16, IL-17, IL-18, IL-19, IL-20, IL-21, IL-22, IL-25, IL-24, IL-25, IL-26, IL-27, IL-28, IL-29, IL-30, IL-31, IL-32, IL-33, IFN-alpha, IFN-beta, IFN-gamma, GM-CSF, G-CSF, M-CSF, LT-beta or TNF-alpha, growth factors, such as hGH.

Further additives which may be included in the inventive vaccine are emulsifiers, such as, for example, Tween®*; wetting agents, such as, for example, sodium lauryl sulfate; colouring agents; taste-imparting agents, pharmaceutical carriers; tablet-forming agents; stabilizers; antioxidants; preservatives.

The inventive composition, in particular the inventive vaccine, can also additionally contain any further compound, which is known to be immune-stimulating due to its binding affinity (as ligands) to human Toll-like receptors TLR1, TLR2, TLR3, TLR4, TLR5, TLR6, TLR7, TLR8, TLR9, TLR10, or due to its binding affinity (as ligands) to murine Toll-like receptors TLR1, TLR2, TLR3, TLR4, TLR5, TLR6, TLR7, TLR8, TLR9, TLR10, TLR11, TLR12 or TLR is.

Another class of compounds, which may be added to an inventive composition, in particular to an inventive vaccine, in this context, may be CpG nucleic acids, in particular CpG-RNA or CpG-DNA. A CpG-RNA or CpG-DNA can be a single-stranded CpG-DNA (ss CpG-DNA), a double-stranded CpG-DNA (dsDNA), a single-stranded CpG-RNA (ss CpG-RNA) or a double-stranded CpG-RNA (ds CpG-RNA). The CpG nucleic acid is preferably in the form of CpG-RNA, more preferably in the form of single-stranded CpG-RNA (ss CpG-RNA). The CpG nucleic acid preferably contains at least one or more (mitogenic) cytosine/guanine dinucleotide sequence(s) (CpG motif(s)). According to a first preferred alternative, at least one CpG motif contained in these sequences, in particular the C (cytosine) and the G (guanine) of the CpG motif, is unmethylated. All further cytosines or guanines optionally contained in these sequences can be either methylated or unmethylated. According to a further preferred alternative, however, the C (cytosine) and the G (guanine) of the CpG motif can also be present in methylated form.

Particularly preferred adjuvants are polyinosinic:polycytidylic acid (also referred to as "poly I:C") and/or its derivative poly-ICLC. Poly I:C is a mismatched double-stranded RNA with one strand being a polymer of inosinic acid, the other a polymer of cytidylic acid. Poly I:C is an immunostimulant known to interact with toll-like receptor s (TLRS). Poly I:C is structurally similar to double-stranded RNA, which is the "natural" stimulant of TLRS. Accordingly, poly I:C may be considered a synthetic analog of double-stranded RNA. Poly-ICLC is a synthetic complex of carboxymethylcellulose, polyinosinic-polycytidylic acid, and poly-L-lysine double-stranded RNA. Similar to poly I:C, also poly-ICLC is a ligand for TLRs. Poly I:C and poly-ICLC typically stimulate the release of cytotoxic cytokines. A preferred example of poly-ICLC is Hiltonol®.

Microbiota Sequence Variant and Medicament Comprising the Same

In a further aspect, the present invention also provides a microbiota sequence variant of a tumor-related antigenic epitope sequence, preferably obtainable by the method for identification of a microbiota sequence variant as described above.

Accordingly, features, definitions and preferred embodiments of the microbiota sequence variant according to the present invention correspond to those described above for the microbiota sequence variant obtained by the method for identification of a microbiota sequence variant. For example, the microbiota sequence variant is preferably a (bacterial) peptide, preferably having a length of 8-12 amino acids, more preferably of 8-10 amino acids, such as nine amino acids, as described above. Moreover, the microbiota sequence variant shares preferably at least 70%, more preferably at least 75%, more preferably at least 80%, even more preferably at least 85%, still more preferably at least 90%, particularly preferably at least 95%, and most preferably at least 99% sequence identity sequence identity with the tumor-related antigenic epitope sequence, as described above. It is also preferred that the core sequence of the microbiota sequence variant is identical with the core sequence of the tumor-related antigenic epitope sequence, wherein the core sequence consists of all amino acids except the three most N-terminal and the three most C-terminal amino acids, as described above. Moreover, the preferred embodiments outlined above for the microbiota sequence variant obtained by the method for identification of a microbiota sequence variant as described above apply accordingly to the microbiota sequence variant according to the present invention.

Specific examples of the microbiota sequence variant according to the present invention include (poly)peptides comprises or consists of an amino acid sequence according to any one of SEQ ID NOs 6-18 and nucleic acid molecules encoding such (poly)peptides. Those examples relate to microbiota sequence variants of epitopes of IL13RA2. The Interleukin-13 receptor subunit alpha-2 (IL-13Ra2 or IL13RA2) is a membrane bound protein that is encoded in humans by the IL13RA2 gene. In a non-exhaustive manner, IL13RA2 has been reported as a potential immunotherapy target (see Beard et al.; Clin Cancer Res; 72(11); 2012). The high expression of IL13RA2 has further been associated with invasion, liver metastasis and poor prognosis in colorectal cancer (Barderas et al.; Cancer Res; 72(11); 2012). Preferably, the microbiota sequence variant according to the present invention comprises or consists of an amino acid sequence according to SEQ ID NO: 6 or 18, or encodes an amino acid sequence according to SEQ ID NO: 6 or 18. More preferably, the microbiota sequence variant according to the present invention comprises or consists of an amino acid sequence according to SEQ ID NO: 18, or encodes an amino acid sequence according to SEQ ID NO: 18.

In a further aspect the present invention also provides a medicament comprising the microbiota sequence variant according to the present invention as described above, which is preferably obtainable by the method for preparation of a medicament according to the present invention as described above.

Accordingly, features, definitions and preferred embodiments of the medicament according to the present invention correspond to those described above for the medicament prepared by the method for preparation of a medicament. For example, the medicament according to the present invention preferably comprises a nanoparticle as described above loaded with the microbiota sequence variant according to the present invention as described above. In particular, such a nanoparticle may be further loaded with an adjuvant as described above. Moreover, the medicament preferably comprises a bacterial cell as described above expressing the microbiota sequence variant according to the present invention.

Preferably, the medicament comprises
(i) the microbiota sequence variant as described above;
(ii) a (recombinant) protein comprising the microbiota sequence variant as described above; (iii) an (immunogenic) compound comprising the microbiota sequence variant as described above;
(iv) a nanoparticle loaded with the microbiota sequence variant as described above; (v) an antigen-presenting cell loaded with the microbiota sequence variant;
(vi) a host cell, such as a bacterial cell as described above, expressing the microbiota sequence variant; or
(vii) a nucleic acid molecule encoding the microbiota sequence variant;
and, optionally, a pharmaceutically acceptable carrier and/or an adjuvant as described above.

Preferably, the medicament is (in the form of/formulated as) a pharmaceutical composition. More preferably, the medicament is a vaccine as described above. Moreover, the preferred embodiments outlined above for the medicament prepared by the method for preparation of a medicament as described above apply accordingly to the medicament according to the present invention.

The inventive composition, in particular the inventive vaccine, may also comprise a pharmaceutically acceptable carrier, adjuvant, and/or vehicle as defined below for the inventive pharmaceutical composition. In the specific context of the inventive composition, in particular of the inventive vaccine, the choice of a pharmaceutically acceptable carrier is determined in principle by the manner in which the inventive composition, in particular the inventive vaccine, is administered. The inventive composition, in particular the inventive vaccine, can be administered, for example, systemically or locally. Routes for systemic administration in general include, for example, transdermal, oral, parenteral routes, including subcutaneous, intravenous, intramuscular, intraarterial, intradermal and intraperitoneal injections and/or intranasal administration routes.

Routes for local administration in general include, for example, topical administration routes but also intradermal, transdermal, subcutaneous, or intramuscular injections or intralesional, intracranial, intrapulmonal, intracardial, intranodal and sublingual injections. More preferably, inventive composition, in particular the vaccines, may be administered by an intradermal, subcutaneous, intranodal or oral. Even more preferably, the inventive composition, in particular the vaccine, may be administered by subcutaneous, intranodal or oral route. Particularly preferably, the inventive composition, in particular the vaccines, may be administered by subcutaneous or oral route. Most preferably, the inventive composition, in particular the vaccines may be administered by oral route. Inventive composition, in particular the inventive vaccines, are therefore preferably formulated in liquid or in solid form.

The suitable amount of the inventive composition, in particular the inventive vaccine, to be administered can be determined by routine experiments with animal models. Such models include, without implying any limitation, rabbit, sheep, mouse, rat, dog and non-human primate models. Preferred unit dose forms for injection include sterile solutions of water, physiological saline or mixtures thereof. The pH of such solutions should be adjusted to about 7.4. Suitable carriers for injection include hydrogels, devices for controlled or delayed release, polylactic acid and collagen matrices. Suitable pharmaceutically acceptable carriers for topical application include those which are suitable for use in lotions, creams, gels and the like. If the inventive composition, in particular the inventive vaccine, is to be administered orally, tablets, capsules and the like are the preferred unit dose form. The pharmaceutically acceptable carriers for the preparation of unit dose forms which can be used for oral administration are well known in the prior art. The choice thereof will depend on secondary considerations such as taste, costs and storability, which are not critical for the purposes of the present invention, and can be made without difficulty by a person skilled in the art.

The inventive pharmaceutical composition as defined above may also be administered orally in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient, i.e. the inventive transporter cargo conjugate molecule as defined above, is combined with emulsifying and suspending agents. If desired, certain sweetening, flavoring or coloring agents may also be added.

The inventive pharmaceutical composition may also be administered topically, especially when the target of treatment includes areas or organs readily accessible by topical application, e.g. including diseases of the skin or of any other accessible epithelial tissue. Suitable topical formulations are readily prepared for each of these areas or organs. For topical applications, the inventive pharmaceutical composition may be formulated in a suitable ointment, containing the inventive immunostimulatory composition, particularly its components as defined above, suspended or dissolved in one or more carriers. Carriers for topical administration include, but are not limited to, mineral oil, liquid petrolatum, white petrolatum, propylene glycol, polyoxyethylene, polyoxypropylene compound, emulsifying wax and water. Alternatively, the inventive pharmaceutical composition can be formulated in a suitable lotion or cream. In the context of the present invention, suitable carriers include, but are not limited to, mineral oil, sorbitan monostearate, polysorbate 60, cetyl esters wax, cetearyl alcohol, 2-octyldodecanol, benzyl alcohol and water.

Sterile injectable forms of the inventive pharmaceutical compositions may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1.3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation of the inventive pharmaceutical composition.

For intravenous, cutaneous or subcutaneous injection, or injection at the site of affliction, the active ingredient will preferably be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as required. Whether it is a polypeptide, peptide, or nucleic acid molecule, other pharmaceutically useful compound according to the present invention that is to be given to an individual, administration is preferably in a "prophylactically effective amount" or a "therapeutically effective amount" (as the case may be), this being sufficient to show benefit to the individual. The actual amount administered, and rate and time-course of administration, will depend on the nature and severity of what is being treated.

In this context, prescription of treatment, e.g. decisions on dosage etc. when using the above medicament is typically within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in REMINGTON'S PHARMACEUTICAL SCIENCES, 16th edition, Osol, A. (ed), 1980.

Accordingly, the inventive pharmaceutical composition typically comprises a "safe and effective amount" of the components of the inventive pharmaceutical composition, in particular of the microbiota sequence variant as defined herein. As used herein, a "safe and effective amount" means an amount of the microbiota sequence variant as defined herein that is sufficient to significantly induce a positive modification of a disease or disorder, i.e. an amount of the microbiota sequence variant as defined herein, that elicits the biological or medicinal response in a tissue, system, animal or human that is being sought. An effective amount may be a "therapeutically effective amount" for the alleviation of the symptoms of the disease or condition being treated and/or a "prophylactically effective amount" for prophylaxis of the symptoms of the disease or condition being prevented. The term also includes the amount of active microbiota sequence variant sufficient to reduce the progression of the disease, notably to reduce or inhibit the tumor growth or infection and thereby elicit the response being sought, in particular such response could be an immune response directed against the microbiota sequence variant (i.e. an "inhibition effective amount"). At the same time, however, a "safe and effective amount" is small enough to avoid serious side-effects, that is to say to permit a sensible relationship between advantage and risk. The determination of these limits typically lies within the scope of sensible medical judgment. A "safe and effective amount" of the components of the inventive pharmaceutical composition, particularly of the microbiota sequence variant as defined above, will furthermore vary in connection with the particular condition to be treated and also with the age and physical condition of the patient to be treated, the body weight, general health, sex, diet, time of administration, rate of excretion, drug combination, the activity of the specific microbiota sequence variant as defined herein, the severity of the condition, the duration of the treatment, the nature of the accompanying therapy, of the particular pharmaceutically acceptable carrier used, and similar factors, within the knowledge and experience of the accompanying doctor. The inventive pharmaceutical composition may be used for human and also for veterinary medical purposes, preferably for human medical purposes, as a pharmaceutical composition in general or as a vaccine.

Pharmaceutical compositions, in particular vaccine compositions, or formulations according to the invention may be administered as a pharmaceutical formulation which can contain the microbiota sequence variant as defined herein in any form described herein.

The terms "pharmaceutical formulation" and "pharmaceutical composition" as used in the context of the present invention refer in particular to preparations which are in such a form as to permit biological activity of the active ingredient(s) to be unequivocally effective and which contain no additional component which would be toxic to subjects to which the said formulation would be administered.

In the context of the present invention, an "efficacy" of a treatment can be measured based on changes in the course of a disease in response to a use or a method according to the present invention. For example, the efficacy of a treatment of cancer can be measured by a reduction of tumor volume, and/or an increase of progression free survival time, and/or a decreased risk of relapse post-resection for primary cancer. More specifically for cancer treated by immunotherapy, assessment of efficacy can be by the spectrum of clinical patterns of antitumor response for immunotherapeutic agents through novel immune-related response criteria (irRC), which are adapted from Response Evaluation Criteria in Solid Tumors (RECIST) and World Health Organization (WHO) criteria (*J. Natl. Cancer Inst.* 2010, 102(18): 1388-1397).

Pharmaceutical compositions, in particular vaccine compositions, or formulations according to the invention may also be administered as a pharmaceutical formulation which can contain antigen presenting cells loaded with microbiota sequence variant according to the invention in any form described herein.

The vaccine and/or the composition according to the present invention may also be formulated as pharmaceutical compositions and unit dosages thereof, in particular together with a conventionally employed adjuvant, immunomodulatory material, carrier, diluent or excipient as described above and below, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous and intradermal) use by injection or continuous infusion.

In the context of the present invention, in particular in the context of a pharmaceutical composition and vaccines according to the present invention, injectable compositions are typically based upon injectable sterile saline or phosphate-buffered saline or other injectable carriers known in the art. Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

Compositions, in particular pharmaceutical compositions and vaccines, according to the present invention may be liquid formulations including, but not limited to, aqueous or oily suspensions, solutions, emulsions, syrups, and elixirs. The compositions may also be formulated as a dry product for reconstitution with water or other suitable vehicle before use. Such liquid preparations may contain additives including, but not limited to, suspending agents, emulsifying agents, non-aqueous vehicles and preservatives. Suspending agents include, but are not limited to, sorbitol syrup, methyl cellulose, glucose/sugar syrup, gelatin, hydroxyethyl cellulose, carboxymethyl cellulose, aluminum stearate gel, and hydrogenated edible fats. Emulsifying agents include, but are not limited to, lecithin, sorbitan monooleate, and acacia. Preservatives include, but are not limited to, methyl or propyl p-hydroxybenzoate and sorbic acid. Dispersing or wetting agents include but are not limited to poly(ethylene glycol), glycerol, bovine serum albumin, Tween®, Span®.

Compositions, in particular pharmaceutical compositions and vaccines, according to the present invention may also be formulated as a depot preparation, which may be administered by implantation or by intramuscular injection.

Compositions, in particular pharmaceutical compositions and vaccines, according to the present invention may also be solid compositions, which may be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, accacia, gelatin, sorbitol, tragacanth, mucilage of starch and polyvinylpyrrolidone. Fillers include, but are not limited to, lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulfate. Tablets may be coated according to methods well known in the art.

Compositions, in particular pharmaceutical compositions and vaccines, according to the present invention may also be administered in sustained release forms or from sustained release drug delivery systems.

Moreover, the compositions, in particular pharmaceutical compositions and vaccines, according to the present invention may be adapted for delivery by repeated administration.

Medical Treatment

In a further aspect the present invention provides the microbiota sequence variant/the medicament as described above for use in the prevention and/or treatment of cancer. Accordingly, the present invention provides a method for preventing and/or treating a cancer or initiating, enhancing or prolonging an anti-tumor response in a subject in need thereof comprising administering to the subject the microbiota sequence variant/the medicament according to the present invention as described above.

The term "cancer", as used herein, refers to a malignant neoplasm. In particular, the term "cancer" refers herein to any member of a class of diseases or disorders that are characterized by uncontrolled division of cells and the ability of these cells to invade other tissues, either by direct growth into adjacent tissue through invasion or by implantation into distant sites by metastasis. Metastasis is defined as the stage in which cancer cells are transported through the bloodstream or lymphatic system.

Preferably, the medicament is administered in combination with an anti-cancer agent, more preferably with an immune checkpoint modulator.

The invention encompasses the administration of the medicament according to the present invention, wherein it is administered to a subject prior to, simultaneously or sequentially with other therapeutic regimens or co-agents useful for treating, and/or stabilizing cancer and/or preventing cancer relapsing (e.g. multiple drug regimens), in a therapeutically effective amount. The medicament according to the present invention can be administered in the same or different composition(s) and by the same or different route(s) of administration as said co-agents.

Said other therapeutic regimens or co-agents may be selected from the group consisting of radiation therapy, chemotherapy, surgery, targeted therapy (including small molecules, peptides and monoclonal antibodies), and anti-angiogenic therapy. Anti-angiogenic therapy is defined herein as the administration of an agent that directly or indirectly targets tumor-associated vasculature. Preferred anti-cancer agents include a chemotherapeutic agent, a targeted drug and/or an immunotherapeutic agent, such as an immune checkpoint modulator.

Traditional chemotherapeutic agents are cytotoxic, i.e. they act by killing cells that divide rapidly, one of the main properties of most cancer cells. Preferred chemotherapeutic agents for combination with the microbiota sequence variant as defined herein are such chemotherapeutic agents known to the skilled person for treatment of cancer. Preferred chemotherapeutic agents for combination include 5-Fluorouracil (5-FU), Capecitabine (Xeloda®), Irinotecan (Camptosar®) and Oxaliplatin (Eloxatin®). It is also preferred that the microbiota sequence variant as defined herein is combined with a combined chemotherapy, preferably selected from (i) FOLFOX (5-FU, leucovorin, and oxaliplatin); (ii) CapeOx (Capecitabine and oxaliplatin); (iii) 5-FU and leucovorin; (iv) FOLFOXIRI (leucovorin, 5-FU, oxaliplatin, and irinotecan); and (v) FOLFIRI (5-FU, leucovorin, and irinotecan). In non-spread cancer, a combination with (i) FOLFOX (5-FU, leucovorin, and oxaliplatin); (ii) CapeOx (Capecitabine and oxaliplatin); or (iii) 5-FU and leucovorin is preferred. For cancer that has spread, a combination with (iv) FOLFOXIRI (leucovorin, 5-FU, oxaliplatin, and irinotecan); (i) FOLFOX (5-FU, leucovorin, and oxaliplatin); or (v) FOLFIRI (5-FU, leucovorin, and irinotecan) is preferred.

Targeted drugs for combination with the microbiota sequence variant as defined herein include VEGF-targeted drugs and EGFR-targeted drugs. Preferred examples of VEGF-targeted drugs include Bevacizumab (Avastin®), ramucirumab (Cyramza®) or ziv-aflibercept (Zaltrap®). Preferred examples of EGFR-targeted drugs include Cetuximab (Erbitux®), panitumumab (Vectibix®) or Regorafenib (Stivarga®).

Immunotherapeutic agents for combination with the microbiota sequence variant as defined herein include vaccines, chimeric antigen receptors (CARs), checkpoint modulators and oncolytic virus therapies.

Preferred vaccines for combination with the microbiota sequence variant as defined herein include TroVax, OncoVax, IMA910, ETBX-011, MicOryx, EP-2101, MKC1106-PP, CDX-1307, V954/V955, MelCancerVac, Imprime PGG, FANG, Tecemotide, AlloStim, DCVax, GI-6301, AVX701, OCV—$Co_2$.

Artificial T cell receptors (also known as chimeric T cell receptors, chimeric immunoreceptors, chimeric antigen receptors (CARs)) are engineered receptors, which graft an arbitrary specificity onto an immune effector cell. Artificial T cell receptors (CARs) are preferred in the context of adoptive cell transfer. To this end, T cells are removed from a patient and modified so that they express receptors specific to the cancer. The T cells, which can then recognize and kill the cancer cells, are reintroduced into the patient.

Preferably, the immune checkpoint modulator for combination with the microbiota sequence variant as defined herein is an activator or an inhibitor of one or more immune checkpoint point molecule(s) selected from CD27, CD28, CD40, CD122, CD137, OX40, GITR, ICOS, A2AR, B7-H3, B7-H4, BTLA, CD40, CTLA-4, IDO, KIR, LAGS, PD-1, TIM-3, VISTA, CEACAM1, GARP, PS, CSF1R, CD94/NKG2A, TDO, GITR, TNFR and/or FasR/DcR3; or an activator or an inhibitor of one or more ligands thereof.

More preferably, the immune checkpoint modulator is an activator of a (co-)stimulatory checkpoint molecule or an inhibitor of an inhibitory checkpoint molecule or a combination thereof.

Accordingly, the immune checkpoint modulator is more preferably (i) an activator of CD27, CD28, CD40, CD122, CD137, OX40, GITR and/or ICOS or (ii) an inhibitor of A2AR, B7-H3, B7-H4, BTLA, CD40, CTLA-4, IDO, KIR, LAGS, PD-1, PDL-1, PD-L2, TIM-3, VISTA, CEACAM1, GARP, PS, CSF1R, CD94/NKG2A, TDO, TNFR and/or FasR/DcR3.

Even more preferably, the immune checkpoint modulator is an inhibitor of an inhibitory checkpoint molecule (but preferably no inhibitor of a stimulatory checkpoint molecule). Accordingly, the immune checkpoint modulator is even more preferably an inhibitor of A2AR, B7-Hs, B7-H4, BTLA, CTLA-4, IDO, KIR, LAG3, PD-1, PDL-1, PD-L2, TIM-3, VISTA, CEACAM1, GARP, PS, CSF1R, CD94/NKG2A, TDO, TNFR and/or DcR3 or of a ligand thereof.

It is also preferred that the immune checkpoint modulator is an activator of a stimulatory or costimulatory checkpoint molecule (but preferably no activator of an inhibitory checkpoint molecule). Accordingly, the immune checkpoint modulator is more preferably an activator of CD27, CD28, CD40, CD122, CD137, OX40, GITR and/or ICOS or of a ligand thereof.

It is even more preferred that the immune checkpoint modulator is a modulator of the CD40 pathway, of the IDO pathway, of the LAGS pathway, of the CTLA-4 pathway and/or of the PD-1 pathway. In particular, the immune checkpoint modulator is preferably a modulator of CD40, LAG3, CTLA-4, PD-L1, PD-L2, PD-1 and/or IDO, more preferably the immune checkpoint modulator is an inhibitor of CTLA-4, PD-L1, PD-L2, PD-1, LAGS, and/or IDO or an activator of CD40, even more preferably the immune checkpoint modulator is an inhibitor of CTLA-4, PD-L1, PD-1, LAG3 and/or IDO, even more preferably the immune checkpoint modulator is an inhibitor of LAG3, CTLA-4 and/or PD-1, and most preferably the immune checkpoint modulator is an inhibitor of CTLA-4 and/or PD-1.

Accordingly, the checkpoint modulator for combination with the microbiota sequence variant as defined herein may be selected from known modulators of the CTLA-4 pathway or the PD-1 pathway. Preferably, the checkpoint modulator for combination with the microbiota sequence variant as defined herein may be selected from known modulators of the the CTLA-4 pathway or the PD-1 pathway. Particularly preferably, the immune checkpoint modulator is a PD-1 inhibitor. Preferred inhibitors of the CTLA-4 pathway and of the PD-1 pathway include the monoclonal antibodies Yervoy® (Ipilimumab; Bristol Myers Squibb) and Tremelimumab (Pfizer/MedImmune) as well as Opdivo® (Nivolumab; Bristol Myers Squibb), Keytruda® (Pembrolizumab; Merck), Durvalumab (MedImmune/AstraZeneca), MEDI4736 (AstraZeneca; cf. WO 2011/066389 A1), MPDL3280A (Roche/Genentech; cf. U.S. Pat. No. 8,217,149 B2), Pidilizumab (CT-011; CureTech), MEDI0680 (AMP-514; AstraZeneca), MSB-0010718C (Merck), MIH1 (Affymetrix) and Lambrolizumab (e.g. disclosed as hPD109A and its humanized derivatives h409A11, h409A16 and h409A17 in WO2008/156712; Hamid et al., 2013; N. Engl. J. Med. 369: L34-144). More preferred checkpoint inhibitors include the CTLA-4 inhibitors Yervoy® (Ipilimumab; Bristol Myers Squibb) and Tremelimumab (Pfizer/MedImmune) as well as the PD-1 inhibitors Opdivo® (Nivolumab; Bristol Myers Squibb), Keytruda® (Pembrolizumab; Merck), Pidilizumab (CT-011; CureTech), MEDI0680 (AMP-514; AstraZeneca), AMP-224 and Lambrolizumab (e.g. disclosed as hPD109A and its humanized derivatives h409A11, h409A16 and h409A17 in WO2008/156712; Hamid 0. et al., 2013; N. Engl. J. Med. 369: 134-144.

It is also preferred that the immune checkpoint modulator for combination with the microbiota sequence variant as defined herein is selected from the group consisting of Pembrolizumab, Ipilimumab, Nivolumab, MPDL3280A, MEDI4736, Tremelimumab, Avelumab, PDR001, LAG525, INCB24360, Varlilumab, Urelumab, AMP-224 and CM-24.

Oncolytic viruses are engineered to cause cell lysis by replicating in tumors, thus activating an antitumor immune response. An oncolytic virus therapy for combination with the microbiota sequence variant as defined herein is preferably selected from the group consisting of JX594 (Thymidine Kinase-Deactivated Vaccinia Virus), ColoAd1 (adenovirus), NV1020 (HSV-derived), ADXS11-001 (attenuated *Listeria* vaccine), Reolysin® (special formulation of the human reovirus), PANVAC (recombinant vaccinia-virus CEA-MUC-1-TRICOM), Ad5-hGCC-PADRE (recombinant adenovirus vaccine) and vvDD-CDSR (vaccinia virus).

Preferably, (i) the microbiota sequence variant and (ii) the chemotherapeutic agent, the targeted drug and/or the immunotherapeutic agent, such as an immune checkpoint modulator, are administered at about the same time.

"At about the same time", as used herein, means in particular simultaneous administration or that directly after administration of (i) the chemotherapeutic agent, the targeted drug and/or the immunotherapeutic agent, such as an immune checkpoint modulator, (ii) the microbiota sequence variant is administered or directly after administration of (i) the microbiota sequence variant (ii) the chemotherapeutic agent, the targeted drug and/or the immunotherapeutic agent, such as an immune checkpoint modulator, is administered. The skilled person understands that "directly after" includes the time necessary to prepare the second administration—in particular the time necessary for exposing and disinfecting the location for the second administration as well as appropriate preparation of the "administration device" (e.g., syringe, pump, etc.). Simultaneous administration also includes if the periods of administration of (i) the microbiota sequence variant and of (ii) the chemotherapeutic agent, the targeted drug and/or the immunotherapeutic agent, such as an immune checkpoint modulator, overlap or if, for example, one component is administered over a longer period of time, such as 30 min, 1 h, 2 h or even more, e.g. by infusion, and the other component is administered at some time during such a long period. Administration of (i) the microbiota sequence variant and of (ii) the chemotherapeutic agent, the targeted drug and/or the immunotherapeutic agent, such as an immune checkpoint modulator, at about the same time is in particular preferred if different routes of administration and/or different administration sites are used.

It is also preferred that (i) the microbiota sequence variant and (ii) the chemotherapeutic agent, the targeted drug and/or the immunotherapeutic agent, such as an immune checkpoint modulator, are administered consecutively. This means that (i) the microbiota sequence variant is administered before or after (ii) the chemotherapeutic agent, the targeted drug and/or the immunotherapeutic agent, such as an immune checkpoint modulator. In consecutive administration, the time between administration of the first component and administration of the second component is preferably no more than one week, more preferably no more than s days, even more preferably no more than 2 days and most preferably no more than 24 h. It is particularly preferred that (i) the microbiota sequence variant and (ii) the chemotherapeutic agent, the targeted drug and/or the immunotherapeutic agent, such as an immune checkpoint modulator, are administered at the same day with the time between administration of the first component (the checkpoint modulator of the microbiota sequence variant) and administration of the second component (the other of the checkpoint modulator and the microbiota sequence variant) being preferably no more than 6 hours, more preferably no more than s hours, even more preferably no more than 2 hours and most preferably no more than 1 h.

Preferably, (i) the microbiota sequence variant and (ii) the chemotherapeutic agent, the targeted drug and/or the immunotherapeutic agent, such as an immune checkpoint modulator, are administered via the same route of administration. It is also preferred that (i) the microbiota sequence variant and (ii) the chemotherapeutic agent, the targeted drug and/or the immunotherapeutic agent, such as an immune checkpoint modulator, are administered via distinct routes of administration.

Moreover, (i) the microbiota sequence variant and (ii) the chemotherapeutic agent, the targeted drug and/or the immunotherapeutic agent, such as an immune checkpoint modulator, are preferably provided in distinct compositions. Alternatively, (i) the microbiota sequence variant and (ii) the chemotherapeutic agent, the targeted drug and/or the immunotherapeutic agent, such as an immune checkpoint modulator, are preferably provided in the same composition.

Accordingly, the present invention provides a pharmaceutical formulation comprising a microbiota sequence variant according to the invention combined with at least one co-agent useful for treating and/or stabilizing a cancer and/or preventing cancer relapsing, and at least one pharmaceutically acceptable carrier.

Moreover, the microbiota sequence variant according to the present invention can be administered after surgery where solid tumors have been removed as a prophylaxis against relapsing and/or metastases.

Moreover, the administration of the imaging or diagnosis composition in the methods and uses according to the invention can be carried out alone or in combination with a co-agent useful for imaging and/or diagnosing cancer.

The present invention can be applied to any subject suffering from cancer or at risk to develop cancer. In particular, the therapeutic effect of said microbiota sequence variant may be to elicit an immune response directed against the reference tumor-related antigenic epitopes, in particular a response that is dependent on CD8+ cytotoxic T cells and/or that is mediated by MHC class I molecules.

In a further aspect the present invention also provides a (in vitro) method for determining whether the microbiota sequence variant of a tumor-related antigenic epitope sequence as described herein is present in an individual comprising the step of determination whether the microbiota sequence variant of a tumor-related antigenic epitope sequence as described herein is present in an (isolated) sample of the individual. Preferably, the (isolated) sample is a stool sample or a blood sample. In this context, the microbiota sequence variant is preferably identified/obtained by a method for identification of a microbiota sequence variant according to the present invention as described herein.

For example, determination of presence of the microbiota sequence variant may be performed on the basis of the detection of microbiota, such as bacteria, harboring the microbiota sequence variant. To this end, a stool sample may be collected and nucleic acids and/or proteins/(poly)peptides may be isolated from the stool sample. The isolated nucleic acids and/or proteins/(poly)peptides may then be sequenced. As an example, the sequencing of the DNA extracted from stool sample could be performed at 40 million pair end reads on an Illumina HiSeq. Sequences can be analyzed using bioinformatics pipeline for identification of genomic part of candidate bacteria expressing the bacterial peptide. Another approach may the single detection of the microbiota sequence variant by using specifically designed PCR primer pairs and real time PCR.

Moreover, determination of presence of the microbiota sequence variant may be performed, for example, on the basis of immune response and/or preexisting memory T cells able to recognize the microbiota sequence variant. To this end, the immune response may be addressed in isolated blood samples for example by co-incubation of the microbiota sequence variant (peptide) with purified peripheral blood mononuclear cells (PBMCs) and evaluation of the immune response by ELISPOT assays. Such assay are well known in the art (Calarota S A, Baldanti F. Enumeration and characterization of human memory T cells by enzyme-linked immunospot assays. Clin Dev Immunol. 2013; 2013: 637649). Alternatively, evaluation of memory T cells and T cell activation by lymphoproliferative response or intracellular staining may be used to determine presence of the microbiota sequence variant or preexisting memory T cells able to recognize the microbiota sequence variant.

Accordingly, the method for preventing and/or treating a cancer or initiating, enhancing or prolonging an anti-tumor response in a subject in need thereof according to the present invention as described above, may further comprise a step of determining whether the microbiota sequence variant of a tumor-related antigenic epitope sequence comprised by the medicament to be administered to the subject is present in the subject. Such determination may be performed as described above.

Preferably, in the method for preventing and/or treating a cancer or initiating, enhancing or prolonging an anti-tumor response in a subject in need thereof according to the present invention as described above, the microbiota sequence variant of a tumor-related antigenic epitope sequence comprised by the medicament to be administered is present in the subject. Without being bound to any theory, it is conceivable that the patient may have memory T-cells primed by the microbiota sequence variant. Existing memory T-cells against the microbiota sequence variant may then be reactivated with a challenge of the administered medicament comprising the microbiota sequence variant and will be strengthened and accelerate establishment of an anti-tumoral response.

It is also preferred that in the method for preventing and/or treating a cancer or initiating, enhancing or prolonging an anti-tumor response in a subject in need thereof according to the present invention as described above, the microbiota sequence variant of a tumor-related antigenic epitope sequence comprised by the medicament to be administered is not present in the subject. Without being bound to any theory, it is conceivable that overexpression of a particular microbiota sequence variant in the gut and very high affinity of the microbiota sequence variant may lead to exhaustion of T cell repertoire able to recognize such a microbiota sequence variant and may reduce clinical efficacy.

EXAMPLES

In the following, particular examples illustrating various embodiments and aspects of the invention are presented. However, the present invention shall not to be limited in scope by the specific embodiments described herein. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become readily apparent to those skilled in the art from the foregoing description, accompanying figures and the examples below. All such modifications fall within the scope of the appended claims.

Example 1: Identification of Bacterial Sequence Variants of Tumor-Related Epitopes in the Human Microbiome 1. Selection of Tumor-Associated (TAA) and Tumor-Specific Antigens (TSA)

According to the classical definition, Tumor-Specific Antigens (TSA) are from antigens (proteins) present only on tumor cells, but not on any other cell type, while Tumor-Associated Antigens (TAA) are present on some tumor cells and also some "normal" (non-tumor) cells. The term "tumor-related antigen", as used herein encompasses, tumor-associated (TAA) as well as tumor-specific antigens (TSA)

Selection of tumor-related proteins/antigens was performed based on literature, in particular based on well-known lists of TAAs and TSAs. For example, large numbers of potential TAA and TSA can be obtained from databases, such as Tumor T-cell Antigen Database ("TANTIGEN"; http://cvc.dfci.harvard.edu/tadb/), Peptide Database (https://www.cancerresearch.org/scientists/events-and-resources/peptide-database) or CTdatabase (http://www.cta.lncc.br/). Data from these database may be manually compared to recent literature in order to identify a feasible tumor-related antigen. For example, literature relating to specific expression of antigens in tumors, such as Xu et al., An integrated genome-wide approach to discover tumor-specific antigens as potential immunologic and clinical targets in cancer. Cancer Res. 2012 Dec. 15; 72(24):6351-61; Cheevers et al., The prioritization of cancer antigens: a national cancer institute pilot project for the acceleration of translational research. Clin Cancer Res. 2009 Sep. 1; 15(17):5323-37, may be useful to prioritize interesting antigens. A list of more than 600 candidate antigens was identified. All selected antigens were annotated regarding expression profile using available tools, such as Gent (http://medicalgenome.kribb.re.kr/GENT/), metabolic gene visualizer (http://merav.wi.mit.edu/), or protein Atlas (https://www.proteinatlas.org/). In addition, for each antigen the potential indication, relation to possible side effects, and driver vs passenger antigens were specified.

Among the 600 antigens, interleukin-13 receptor subunit alpha-2 (IL-13Ra2 or IL13RA2) was selected based on the facts that (i) it comprises an epitope identified as a CTL (cytotoxic T lymphocyte) epitope (Okano F, Storkus W J, Chambers W H, Pollack I F, Okada H. Identification of a novel HLA-A*0201-restricted, cytotoxic T lymphocyte epitope in a human glioma-associated antigen, interleukin is receptor alpha2 chain. Clin Cancer Res. 2002 September; 8(9): 2851-5); (ii) IL13RA2 is referenced in Tumor T-cell Antigen Database and CT database as an overexpressed gene in brain tumor; (iii) overexpression and selective expression of IL13RA2 was confirmed with tools as Gent, Metabolic gene visualizer and protein atlas, analyzing data from gene expression (microarrays studies); and (iv) overexpression was also reported in literature in brain tumors (Debinski et al., Molecular expression analysis of restrictive receptor for interleukin 13, a brain tumor-associated cancer/testis antigen. Mol Med. 2000 May; 6(5):440-9), in head and neck tumors (Kawakami et al., Interleukin-13 receptor alpha2 chain in human head and neck cancer serves as a unique diagnostic marker. Clin Cancer Res. 2003 Dec. 15; 9(17):6381-8) and in melanoma (Beard et al., Gene expression profiling using nanostring digital RNA counting to identify potential target antigens for melanoma immunotherapy. Clin Cancer Res. 2013 Sep. 15; 19(18):4941-50).

In particular, confirmation of overexpression and selective expression of IL13RA2 (point (iii)) was performed as follows: Analysis of mRNA data from the tissue atlas (RNA-seq data 37 normal tissues and 17 cancer types) generated by "The Cancer Genome Atlas" (TCGA; available at https://cancergenome.nih.gov/)) highlight the low basal level of IL13RA2 mRNA in normal tissue (with the exception of testis) and the high level of IL13RA2 mRNA expression in several tumor types with the highest expression observed in glioma samples. The same was observed when IL13RA2 mRNA expression was performed using Metabolic gEne RApid Visualizer (available at http://merav.wi.mit.edu/, analyzing data from the International Genomic Consortium, and NCBI GEO dataset) with a very low basal expression in most of the normal tissues tested, except for testis) and a strong expression in melanoma samples, glioblastoma and some samples of thyroid and pancreatic primary tumors.

IL13RA2 is a membrane bound protein that is encoded in humans by the IL13RA2 gene. In a non-exhaustive manner, IL13RA2 has been reported as a potential immunotherapy target (see Beard et al.; Clin Cancer Res; 72(11); 2012). The high expression of IL13RA2 has further been associated with invasion, liver metastasis and poor prognosis in colorectal cancer (Barderas et al.; Cancer Res; 72(11); 2012). Thus IL i3RA2 could be considered as a driver tumor antigen.

2. Selection of One or More Epitopes of Interest in the Selected Tumor-Related Antigen In the next step, epitopes of the selected tumor-related antigen, which are presented specifically by MHC-I, were identified. To this end, the tumor-related antigen sequence (of IL13RA2) was analyzed by means of "Immune epitope database and analysis resource" (IEDB; http://www.iedb.org/; for MHC-I analysis in particular: http://tools.immuneepitope.org/analyze/html/mhcprocessing.html—as used for IL13RA2 analysis, see also http://tools.immuneepitope.org/processing/) combining proteasomal cleavage, TAP transport, and MHC class I analysis tools for prediction of peptide presentation. Namely, the protein sequence of IL13RA2 was submitted to that IEDB analysis tool for identification of potential epitopes that could be presented by HLA.A2.1. Thereby, a list of 371 potential epitopes with HLA A2.1 binding properties was obtained. Two epitopes of that list were previously described as potential epitopes: WLPFGFILI (SEQ ID NO: 1) that was described and functionally validated by Okano et al. (Okano F, Storkus W J, Chambers W H, Pollack I F, Okada H. Identification of a novel HLA-A*0201-restricted, cytotoxic T lymphocyte epitope in a human glioma-associated antigen, interleukin is receptor alpha2 chain. Clin Cancer Res. 2002 September;8(9): 2851-5) and LLDTNYNLF (SEQ ID NO: 2) that was reported in IEDB database as found in a melanoma peptidome study (Gloger et al., Mass spectrometric analysis of the HLA class I peptidome of melanoma cell lines as a promising tool for the identification of putative tumor-associated HLA epitopes. Cancer Immunol Immunother. 2016 November; 65(11):1577-1593).

In order to identify epitopes, which have a good chance to be efficiently presented by MHC at the surface of tumor cells, in the list of the 371 potential epitopes with HLA A2.1 binding properties, in silico affinity of the 371 candidate epitopes to HLA A2.1 was calculated using the NetMHCpan 3.0 tool (http://www.cbs.dtu.dk/services/NetMHCpan/), with a maximum accepted affinity of 3000 nM (IC50). Thereby, a list of 54 IL13RA2 epitopes was obtained.

3. Identification of Bacterial Sequence Variants of the Selected Epitopes in the Human Microbiome Finally, the 54 selected IL13RA2-epitopes were compared to the "Integrated reference catalog of the human gut microbiome" (available at http://meta.genomics.cn/meta/home) in order to identify microbiota sequence variants of the 54 selected human IL13RA2-epitopes. To this end, a protein BLAST search (blastp) was performed using the "PAM-30" protein substitution matrix, which describes the rate of amino acid changes per site over time, and is recommended for queries with lengths under 35 amino acids; with a word size of 2, also suggested for short queries; an Expect value (E) of 20000000, adjusted to maximize the number of possible matches; the composition-based-statistics set to '0', being the input sequences shorter than so amino acids, and allowing only un-gapped alignments. Thereafter, the blastp results were filtered to obtain exclusively microbial peptide sequences with a length of 9 amino acids (for binding to HLA-A2.1), admitting mismatches only at the beginning and/or end of the human peptide, with a maximum of two mismatches allowed per sequence. Thereby, a list of 514 bacterial sequences (nonapeptides, as a length of nine amino acid was used as a filter) was obtained, which consists of bacterial sequence variants of the selected IL13RA2 epitopes in the human microbiome.

Example 2: Testing Binding of Selected Bacterial Sequence Variants to MHC

As binding of microbial mimics to MHC molecules is essential for antigen presentation to cytotoxic T-cells, affinity of the 514 bacterial sequences to MHC class I HLA.A2.01 was calculated using the NetMHCpan 3.0 tool (http://www.cbs.dtu.dk/services/NetMHCpan/). This tool is trained on more than 180000 quantitative binding data covering 172 MHC molecules from human (HLA-A, B, C, E) and other species. The 514 bacterial sequences (blastp result of Example 1) were used as input, and the affinity was predicted by setting default thresholds for strong and weak binders. The rank of the predicted affinity compared to a set of 400000 random natural peptides was used as a measure of the binding affinity. This value is not affected by inherent bias of certain molecules towards higher or lower mean predicted affinities. Very strong binders are defined as having % rank <0.5, strong binders are defined as having % rank ≥0.5 and <1.0, moderate binders are defined as having % rank of ≥1.0 and ≤2.0 and weak binders are defined as having % rank of <2.0. Namely, from the 514 bacterial sequences, only those were selected, which show a very strong affinity (% rank <0.5), and where the human reference epitope shows at least strong affinity (for human peptide) (% rank <1).

Thereby, the following 13 bacterial sequence variants (Peptide 1-Peptide 13 were identified (Table 3):

| Bacterial peptide, SEQ ID # | Human reference epitope, SEQ ID # | Affinity human peptide % rank | Affinity human peptide [nM] | Affinity bacterial peptide % rank | Affinity bacterial peptide [nM] |
|---|---|---|---|---|---|
| 6 | 3 | 1.3 | 143.467 | 0.18 | 13.5048 |
| 7 | 3 | 1.3 | 143.467 | 0.06 | 6.6623 |
| 8 | 3 | 1.3 | 143.467 | 0.20 | 16.0441 |
| 9 | 4 | 0.5 | 35.5261 | 0.01 | 2.8783 |
| 10 | 4 | 0.5 | 35.5261 | 0.02 | 3.6789 |
| 11 | 4 | 0.5 | 35.5261 | 0.04 | 5.0586 |
| 12 | 4 | 0.5 | 35.5261 | 0.05 | 5.8467 |
| 13 | 4 | 0.5 | 35.5261 | 0.18 | 13.3325 |
| 14 | 4 | 0.5 | 35.5261 | 0.40 | 25.3124 |
| 15 | 5 | 0.09 | 8.0315 | 0.04 | 5.5211 |
| 16 | 5 | 0.09 | 8.0315 | 0.40 | 26.9535 |
| 17 | 5 | 0.09 | 8.0315 | 0.40 | 26.9535 |
| 18 | 1 | 0.8 | 66.1889 | 0.08 | 7.4445 |

Example 3: Determining Annotation and Cellular Localization of the Bacterial Proteins Comprising the Selected Bacterial Sequence Variants Next, the annotation of the bacterial proteins containing the selected bacterial epitope sequence variants was performed. To this end, a blast-based comparison against both the Kyoto Encyclopedia of Genes and Genomes (KEGG) (http://www.genome.jp/kegg/) and the National Center for Biotechnology Information (NCBI) Reference Sequence Database (RefSeq) (https://www.ncbi.nlm.nih.gov/refseq/). RefSeq provides an integrated, non-redundant set of sequences, including genomic DNA, transcripts, and proteins. In KEGG, the molecular-level functions stored in the KO (KEGG Orthology) database were used. These functions are categorized in groups of orthologues, which contain proteins encoded by genes from different species that evolved from a common ancestor.

In a next step, a prediction of the cellular localization of the bacterial proteins containing the selected bacterial epitope sequence variants was performed using two different procedures, after which a list of the peptide-containing proteins with the consensus prediction is delivered. First, a dichotomic search strategy to identify intracellular or extracellular proteins based on the prediction of the presence of a signal peptide was carried out. Signal peptides are ubiquitous protein-sorting signals that target their passenger protein for translocation across the cytoplasmic membrane in prokaryotes. In this context both, the SignalP 4.1. (www.cbs.dtu.dk/services/SignalP) and the Phobius server (phobius.sbc.su.se) were used to deliver the consensus prediction. If the presence of a signal peptide was detected by the two approaches, it was interpreted that the protein is likely to be extracellular or periplasmic. If not, the protein probably belongs to the outer/inner membrane, or is cytoplasmic. Second, a prediction of the transmembrane topology is performed. Both signal peptides and transmembrane domains are hydrophobic, but transmembrane helices typically have longer hydrophobic regions. SignalP 4.1. and Phobius have the capacity to differentiate signal peptides from transmembrane domains. A minimum number of 2 predicted transmembrane helices is set to differentiate between membrane and cytoplasmic proteins to deliver the final consensus list. Data regarding potential cellular localization of the bacterial protein is of interest for selection of immunogenic peptides, assuming that secreted components or proteins contained in secreted exosomes are more prone to be presented by APCs.

TABLE 4 shows the SEQ ID NOs of the bacterial proteins containing the 13 bacterial peptides shown in Table 4, their annotation and cellular localization

| Bacterial peptide, SEQ ID # | Bacterial protein SEQ ID # | Phylum | Genus | Species | Kegg orthology | Consensus cellular localization |
|---|---|---|---|---|---|---|
| 6 | 19 | Firmicutes | *Lachnoclostridium* | *Lachnoclostridium phytofermentans* | K01190 | No transmembrane |
| 7 | 20 | unknown | unknown | unknown | unknown | No transmembrane |
| 8 | 21 | Firmicutes | *Lactobacillus* | unknown | unknown | Transmembrane |
| 9 | 22 | unknown | unknown | unknown | unknown | No transmembrane |
| 10 | 23 | Firmicutes | *Ruminococcus* | *Ruminococcus* sp. 5_1_39BFAA | K07315 | No transmembrane |
| 11 | 24 | unknown | unknown | unknown | unknown | No transmembrane |
| 12 | 25 | Firmicutes | unknown | unknown | K19002 | No transmembrane |
| 13 | 26 | Bacteroidetes | *Bacteroides* | *Bacteroides fragilis* | unknown | No transmembrane |
| 14 | 27 | unknown | unknown | unknown | K01992 | Transmembrane |
| 15 | 28 | Firmicutes | *Coprobacillus* | *Coprobacillus* sp. 8_1_38FAA | K07636 | No transmembrane |
| 16 | 29 | unknown | unknown | unknown | unknown | No transmembrane |

TABLE 4-continued shows the SEQ ID NOs of the bacterial proteins containing the 13 bacterial peptides shown in Table 4, their annotation and cellular localization

| Bacterial peptide, SEQ ID # | Bacterial protein SEQ ID # | Phylum | Genus | Species | Kegg orthology | Consensus cellular localization |
|---|---|---|---|---|---|---|
| 17 | 30 | unknown | unknown | unknown | unknown | No trans-membrane |
| 18 | 31 | unknown | unknown | unknown | K19427 | Trans-membrane |

Based on the data shown in Tables s and 4, the bacterial peptide according to SEQ ID NO: 18 (amino acid sequence: FLPFGFILV; also referred herein as "IL13RA2-B"), which is a sequence variant of the human IL13RA2 reference epitope according to SEQ ID NO: 1 (WLPFGFILI, see Table 2; also referred herein as "IL13RA2-H"), was selected for further studies. Effectively, the human reference epitope has intermediate affinity, and is presented at the surface of tumor cells. This MHC presentation was confirmed in several published studies (Okano et al., Identification of a novel HLA-A*0201-restricted, cytotoxic T lymphocyte epitope in a human glioma-associated antigen, interleukin is receptor alpha2 chain. Clin Cancer Res. 2002 September; 8(9):2851-5).

The bacterial sequence variant (SEQ ID NO: 18) has a very strong binding affinity for HLA.A2.01. Furthermore, this bacterial peptide sequence variant is comprised in a bacterial protein, which is predicted to be expressed at the transmembrane level, thereby increasing the probability of being part of exosome that will be trapped by antigen-presenting cells (APC) for MHC presentation.

Example 4: Bacterial Peptide IL13RA2-B (SEQ ID NO: 18) has Superior Affinity to the HLA-A*0201 Allele In Vitro than the Human Epitope IL13RA2-H (SEQ ID NO: 1)

This Example provides evidence that the bacterial peptide of sequence SEQ ID NO: 18 (FLPFGFILV; also referred herein as "IL13RA2-B") has high affinity to the HLA-A*0201 allele in vitro, whereas the corresponding reference human peptide derived from IL13RA2 (WLPFGFILI, SEQ ID NO: 1, also referred herein as "IL13RA2-H") has low affinity.

A. Materials and Methods
A1. Measuring the Affinity of the Peptide to T2 Cell Line.

The experimental protocol is similar to the one that was validated for peptides presented by the HLA-A*0201 (Tourdot et al., A general strategy to enhance immunogenicity of low-affinity HLA-A2.1-associated peptides: implication in the identification of cryptic tumor epitopes. Eur J Immunol. 2000 December; 50(12):3411-21). Affinity measurement of the peptides is achieved with the human tumoral cell T2 which expresses the HLA-A*0201 molecule, but which is TAP 1/2 negative and incapable of presenting endogenous peptides.

T2 cells ($2.10^5$ cells per well) were incubated with decreasing concentrations of peptides from 100 µM to 0.1 µM in a AIMV medium supplemented with 100 ng/µl of human β2m at 37° C. for 16 hours. Cells were then washed two times and marked with the anti-HLA-A2 antibody coupled to PE (clone BB7.2, BD Pharmagen).

The analysis was performed by FACS (Guava Easy Cyte). For each peptide concentration, the geometric mean of the labelling associated with the peptide of interest was subtracted from background noise and reported as a percentage of the geometric mean of the HLA-A*0202 labelling obtained for the reference peptide HIV pol 589-597 at a concentration of 100 µM. The relative affinity is then determined as follows:

relative affinity=concentration of each peptide inducing 20% of expression of HLA-A*0201/concentration of the reference peptide inducing 20% of expression of HLA-A*0201.

A2. Solubilisation of Peptides

Each peptide was solubilized by taking into account the amino acid composition. For peptides which do not include any cysteine, methionine, or tryptophan, the addition of DMSO is possible to up to 10% of the total volume. Other peptides are re-suspended in water or PBS pH7.4.

B. Results

For T2 Cells: Mean fluorescence intensity for variable peptidic concentrations: Regarding the couple IL13RA2 peptides (IL13RA2-H and IL13RA2-B), the human peptide does not bind to HLA-A*0201, whereas the bacterial peptide IL13RA2-B binds strongly to HLA-A*0201: 112.05 vs 18.64 at 100 µM; 40.77 vs 11.61 at 10 µM; 12.18 vs 9.41 at 1 µM; 9.9 vs 7.46 at 0.1 µM. Also, IL13RA2-B at 4.4 µM induces 20% of expression of the HLA-A*0201 (vs 100 µM for IL13RA2-H).

Similar results were obtained from a second distinct T2 cell clone.

Example 5: Bacterial Peptide IL13RA2-B (SEQ ID NO: 18) has Superior Affinity to the HLA-A*0201 Allele In Vitro This Example provides evidence that the bacterial peptide of sequence SEQ ID NO: 18 (FLPFGFILV; also referred herein as "IL13RA2-B") has higher affinity to the HLA-A*0201 allele than other sequence variants of the corresponding reference human peptide derived from IL13RA2 (WLPFGFILI, SEQ ID NO: 1, also referred herein as "IL13RA2-H"). In this experiment, the bacterial peptide of sequence SEQ ID NO: 18 (FLPFGFILV; also referred herein as "IL13RA2-B") was compared to the peptide "1A9V", as described by Eguchi Junichi et al., 2006, Identification of interleukin-13 receptor alpha 2 peptide analogues capable of inducing improved anti-glioma CTL responses. Cancer Research 66(11): 5883-5891, in which the tryptophan at position 1 of SEQ ID NO: 1 was substituted by alanine (IA) and the isoleucine at position 9 of SEQ ID NO: 1 was substituted by valine (9V);

peptide "119A", wherein the tryptophan at position 1 of SEQ ID NO: 1 was substituted by isoleucine (1I) and the isoleucine at position 9 of SEQ ID NO: 1 was substituted by alanine (9A); and peptide "1F9M", wherein the tryptophan at position 1 of SEQ ID NO: 1 was substituted by phenylalanine (IF) and the isoleucine at position 9 of SEQ ID NO: 1 was substituted by methionine (9M).

A. Materials and Methods

The experimental protocol, materials and methods correspond to those outlined in Example 4, with the only difference that the above mentioned antigenic peptides were used.

B. Results

The following in vitro binding affinities were obtained (Table 5):

| Peptide | In vitro binding affinity |
|---|---|
| IL13RA2-B (SEQ ID No 18) | 0.49 |
| 1A9V | 3.06 |
| 1I9A | 2.22 |
| 1F9M | 2.62 |

Accordingly, the antigenic peptide according to the present invention (IL13RA2-B (SEQ ID N°31)) showed considerably higher binding affinity to HLA-A*0201 than all other peptides tested, whereas the peptide "1A9V", as described by Eguchi Junichi et al., 2006, Identification of interleukin-13 receptor alpha 2 peptide analogues capable of inducing improved antiglioma CTL responses. Cancer Research 66(11): 5883-5891, showed the lowest affinity of the peptides tested.

Example 5: Vaccination of Mice with the Bacterial Peptide IL13RA4-B (SEQ ID NO: 18) Induces Improved T Cell Responses in a ELISPOT-IFNγ Assay A. Materials and Methods
A.1 Mouse Model The features of the model used are outlined in Table 6:

| | |
|---|---|
| Mouse | C57BL/6J B2m $^{tm1Unc}$IAb$^{-/-}$ Tg(HLA-DRA |
| Model | HLA-DRB1*0301)$^{\#Gjh}$ Tg(HLA-A/H2-D/B2M)$^{1Bpe}$ |
| Acronym | β/A2/DR3 |
| Description | Immunocompetent, no mouse class 1 and class II MHC |
| Housing | SOPF conditions (ABSL3) |
| Number of mice | 24 adults (>8 weeks of age) |

These mice have been described in several reports (Koller et al., Normal development of mice deficient in beta 2M, MHC class I proteins, and CD8+ T cells. Science. 1990 Jun. 8; 248(4960):1227-so. Cosgrove et al., Mice lacking MHC class II molecules. Cell. 1991 Sep. 6; 66(5):1051-66; Pascolo et al., HLA-A2.1-restricted education and cytolytic activity of CD8(+) T lymphocytes from beta2 microglobulin (beta2m) HLA-A2.1 monochain transgenic H-2Db beta2m double knockout mice. J Exp Med. 1997 Jun. 16; 185(12): 2045-51).

A.2. Immunization Scheme.

The immunization scheme is shown in FIG. 1. Briefly, 14 β/A2/DR3 mice were assigned randomly (based on mouse sex and age) to two experimental groups, each immunized with a specific vaccination peptide (vacc-pAg) combined to a common helper peptide (h-pAg) (as outlined in Table 7 below). The vacc-pAg were compared in couples (group 1 vs. group 2). Thereby, both native and optimized versions of a single peptide were compared in each wave.

TABLE 7

Experimental group composition. h-pAg: 'helper' peptide; vacc-pAg: vaccination peptide. The number of boost injections is indicated into brackets.

| Group | Peptide (vacc-pAg) | Helper (h-pAg) | Prime | Boost | Animal number |
|---|---|---|---|---|---|
| 1 | IL13RA2-B (100 μg) SEQ ID No 18 | HHD-DR3 (150 μg) SEQ ID No 32 | + | +(1X) | 6 |
| 2 | IL13RA2-H (100 μg) SEQ ID No 1 | HHD-DR3 (150 μg) SEQ ID No 32 | + | +(1X) | 6 |

The peptides were provided as follows:
couples of vacc-pAg: IL13RA2-H and IL13RA2-B; all produced and provided at a 4 mg/ml (4 mM) concentration;
h-pAg: HHD-DRs peptide (SEQ ID NO: 52); provided lyophilized (50.6 mg; Eurogentec batch 1611166) and re-suspended in pure distilled water at a 10 mg/mL concentration.

The animals were immunized on day o (do) with a prime injection, and on d14 with a boost injection. Each mouse was injected s.c. at tail base with 100 μL of an oil-based emulsion that contained:
100 μg of vacc-pAg (25 μL of 4 mg/mL stock per mouse);
150 μg of h-pAg (15 μL of 10 mg/mL stock per mouse);
10 μL of PBS to reach a total volume of 50 μL (per mouse);
Incomplete Freund's Adjuvant (IFA) added at 1:1 (v:v) ratio (50 μL per mouse).

A separate emulsion was prepared for each vacc-pAg, as follows: IFA reagent was added to the vacc-pAg/h-pAg/PBS mixture in a 15 mL tube and mixed on vortex for repeated cycles of 1 min until forming a thick emulsion.

A.3. Mouse Analysis

Seven days after the boost injection (i.e. on d21), the animals were euthanized and the spleen was harvested. Splenocytes were prepared by mechanical disruption of the organ followed by 70 μm-filtering and Ficoll density gradient purification.

The splenocytes were immediately used in an ELISPOT-IFNγ assay (Table 8). Experimental conditions were repeated in quadruplets, using 2*10⁵ total splenocytes per well, and were cultured in presence of vacc-pAg (10 μM), Concanavalin A (ConA, 2.5 μg/mL) or medium-only to assess for their capacity to secrete IFNγ. The commercial ELISPOT-IFNγ kit (Diaclone Kit Mujrine IFNγ ELISpot) was used following the manufacturer's instructions, and the assay was performed after about 16 h of incubation.

TABLE 8

Setup of the ELISPOT-IFNγ assay.

| Group | Stimulus | Wells | Animal | Total |
|---|---|---|---|---|
| 1 | IL13RA2-B (10 μM) SEQ ID No 18 | 4 | 6 | 24 |
| | IL13RA2-H (10 μM) SEQ ID No 1 | 4 | 6 | 24 |
| | ConA (2.5 μg/ml) | 4 | 6 | 24 |
| | Medium | 4 | 6 | 24 |
| 2 | IL13RA2-B (10 μM) SEQ ID No 18 | 4 | 6 | 24 |
| | IL13RA2-H (10 μM) SEQ ID No 1 | 4 | 6 | 24 |
| | ConA (2.5μg/ml) | 4 | 6 | 24 |
| | Medium | 4 | 6 | 24 |

Spots were counted on a Grand ImmunoSpot® S6 Ultimate UV Image Analyzer interfaced to the ImmunoSpot 5.4 software (CTL-Europe). Data plotting and statistical analysis were performed with the Prism-5 software (GraphPad Software Inc.).

The cell suspensions were also analyzed by flow cytometry, for T cell counts normalization. The monoclonal antibody cocktail (data not shown) was applied on the purified leucocytes in presence of Fc-block reagents targeting murine (1:10 diluted 'anti-mCD16/CD32 CF11 clone'—internal source) Fc receptors. Incubations were performed in 96-well plates, in the dark and at 4° C. for 15-20 minutes. The cells were washed by centrifugation after staining to remove the excess of monoclonal antibody cocktail, and were re-suspended in PBS for data acquisition.

All data acquisitions were performed with an LSR-II Fortessa flow cytometer interfaced with the FACS-Diva software (BD Bioscience). The analysis of the data was performed using the FlowJo-9 software (TreeStar Inc.) using a gating strategy (not shown).

TABLE 9

FACS panel EXP-1.

| Target | Label | Clone | Provider | Dilution |
|---|---|---|---|---|
| mCD3εγ | FITC | 145-2C11 | Biolegend | 1/100 |
| mCD4 | PE | RM4-5 | Biolegend | 1/100 |
| mCD8α | APC | 53-6.7 | Biolegend | 1/100 |

B. Results

A total of 14 P/A2/DR3 mice were used for this experiment (see Table 8). At time of sacrifice, the spleen T cell population was analysed by flow cytometry, showing that the large majority belonged to the CD4+ T cell subset.

TABLE 10

Individual mouse features (groups 1 & 2). Each mouse is identified by a unique ear tag ID number.

| Mouse ID | Sex | Age[a] (wks) | Group (pAg) | T cells[b] (%) | T4[c] (%) | T8[c] (%) | Note[d] |
|---|---|---|---|---|---|---|---|
| 826 | M | 14 | 1 (IL13RA2-B) | 18.6 | 72.0 | 13.7 | P1/2 |
| 827 | M | 14 | 1 (IL13RA2-B) | 21.1 | 82.5 | 8.7 | P1/2 |
| 828 | M | 14 | 1 (IL13RA2-B) | 20.9 | 78.4 | 8.6 | P1/2 |
| 829 | F | 15 | 1 (IL13RA2-B) | 23.8 | 67.0 | 17.5 | P1/2 |
| 830 | F | 15 | 1 (IL13RA2-B) | 29.2 | 73.3 | 12.5 | P1/2 |
| 831 | F | 15 | 1 (IL13RA2-B) | N.A. | N.A. | N.A. | ID tag lost (excluded) |
| 17 | M | 9 | 1 (IL13RA2-B) | 8.3 | 83.7 | 10.4 | P5 |
| 832 | F | 15 | 2 (IL13RA2-H) | 28.3 | 83.4 | 5.7 | P1/2 |
| 833 | F | 15 | 2 (IL13RA2-H) | N.A. | N.A. | N.A. | ID tag lost (excluded) |
| 834 | F | 15 | 2 (IL13RA2-H) | 27.5 | 79.7 | 7.2 | P1/2 |
| 835 | M | 13 | 2 (IL13RA2-H) | 33.8 | 84.2 | 8.5 | P1/2 |
| 836 | M | 13 | 2 (IL13RA2-H) | 31.4 | 84.7 | 6.3 | P1/2 |
| 837 | M | 15 | 2 (IL13RA2-H) | 30.8 | 83.4 | 5.4 | P1/2 |
| 18 | M | 9 | 2 (IL13RA2-H) | 11.2 | 85.9 | 9.2 | P5 |

[a]age at onset of the vaccination protocol (in weeks);
[b]percentage of T cells in total leukocytes;
[c]percentage of CD4+ or CD8+ cells in total T cells;
[d]plate (P) number.

After plating and incubation with the appropriate stimuli, the IFNγ-producing cells were revealed and counted. The data were then normalized as a number of specific spots (the average counts obtained in the 'medium only' condition being subtracted) per $10^6$ total T cells.

The individual average values (obtained from the quadruplicates) were next used to plot the group average values (see FIG. 3A). As the functional capacity of T cells might vary from individual to individual, the data were also expressed as the percentage of the ConA response per individual (see FIG. 3B).

Overall, vaccination with the IL13RA2-B pAg bacterial peptide induced improved T cell responses in the ELISPOT-IFNγ assay, as compared to IL13RA2-H pA (reference human)-vaccinated animals (group 2). For group 1 (IL13RA2-B), ex vivo re-stimulation with the IL13RA2-B pAg promoted higher response than with the IL13RA2-H pAg. It was not the case for group 2 (IL13RA2-H). The percentage of ConA-induced response (mean+/−SEM) for each condition was as follows:

Group 1 (IL13RA2-B)/IL13RA2-B pAg: 56.3%+/−18.1
Group 1 (IL13RA2-B)/IL13RA2-H pAg: 32.3%+/−11.8
Group 2 (IL13RA2-H)/IL13RA2-B pAg: 2.0%+/−0.8
Group 2 (IL13RA2-H)/IL13RA2-H pAg: 1.1%+/−0.8

Accordingly, those results provide experimental evidence that tumor-antigen immunotherapy targeting IL13RA2 is able to improve T cell response in vivo and that the IL13RA2-B bacterial peptide (SEQ ID NO: 18), which was identified as outlined in Examples 1-3, is particularly efficient for that purpose.

Example 6: Bacterial Peptide IL13RA4-B (SEQ ID NO: 18) Provides in Vitro Cytotoxicity Against Tumor Cells This Example provides evidence that the bacterial peptide of sequence SEQ ID NO: 18 (FLPFGFILV; also referred herein as "IL13RA2-B") provides in vitro cytotoxicity against U87 cells, which are tumor cells expressing IL13RA2. In contrast, the corresponding reference human peptide derived from IL13RA2 (WLPFGFILI, SEQ ID NO: 1, also referred herein as "IL13RA2-H") does not provide in vitro cytotoxicity against U87 cells.

Methods:

Briefly, CD8 T cells from mice immunized with IL13RA2-H or IL13RA2-H were used. These cells were obtained after sorting of splenocyte from immunized mice and were placed on top of U87 cells (tumor cells expressing IL13RA2).

In more detail, CD3+ T cells were purified from splenocytes of HHD mice immunized with IL13RA2-H (WLPFG-FILI, SEQ ID NO: 1) or IL13RA2-B (FLPFGFILV, SEQ ID NO: 18). To this end, B6 β2 m$^{ko}$ HHD/DR3 mice were injected s.c. at tail base with 100 μL of an oil-based emulsion containing vaccination peptide plus helper peptide plus CFA (complete Freund's adjuvant), at day 0 and day 14 as described in Example 5. On d21, i.e. seven days after the boost injection, the animals were euthanized and the spleen was harvested. Splenocytes were prepared by mechanical disruption of the organ. CD3+ purification was performed using the mouse total T cells isolation kit from Miltenyi biotec using the recommended procedure. Efficient purification of cells and viability was validated by cytometry using appropriate marker for viability, CD8, CD4, CD3, and CD45.

U87-MG cells were seeded at 6×10$^5$ cells/well in flat-bottomed 24-well culture plates and incubated for 24 h at 37° C. in DMEM (Dulbecco's Modified Eagle Medium) containing 10% of FCS (fetal calf serum) and antibiotics. After 24 hours, culture media were removed and replaced with media containing purified T CD3+ cells. The following ratios of T cells vs. U87-MG cells were used: 1/0.5, 1/1 and 1/5. 72 hours after co-culture of U87-MG cells and CD3+ T cells, all cells from the wells were harvested and specific U87-MG cell death was evaluated after immunostaining of CD45 negative cells with DAPI and fluorescent annexin V followed by cytometry analysis.

Figure 3:
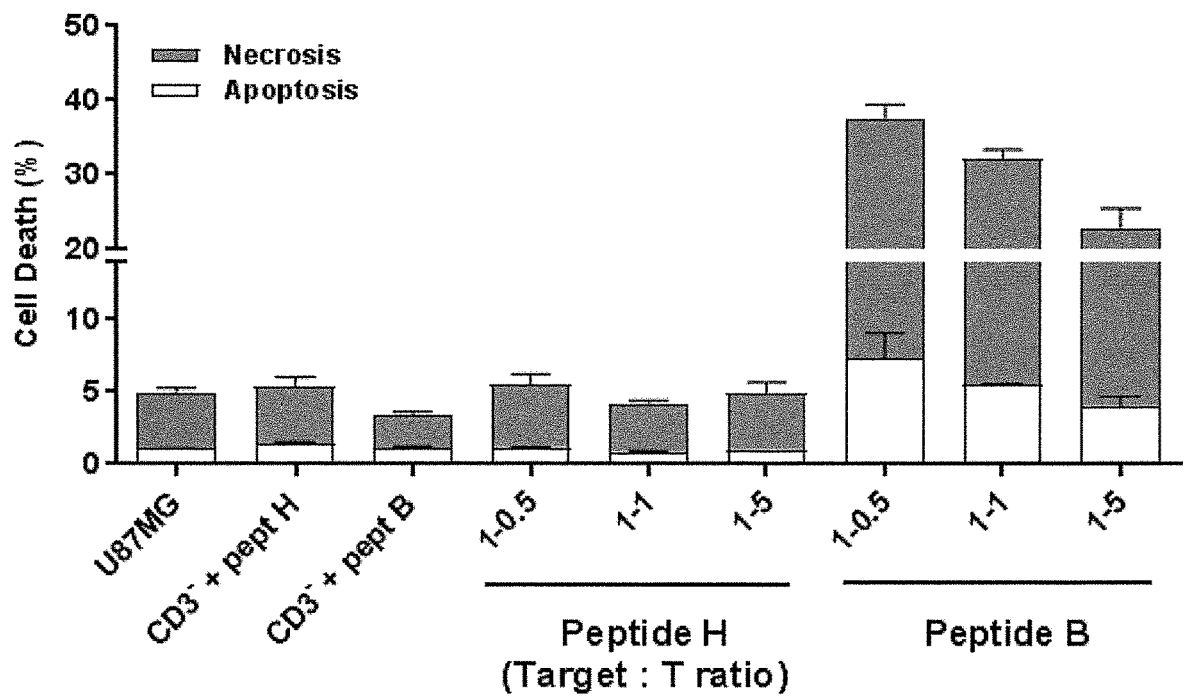
FIG. 3 shows the results of Example 6.

Results:

Results are shown in FIG. 3. In general, U87 cell lysis was observed after treatment with IL13RA2-B but not with IL13RA2-H.

TABLE OF SEQUENCES AND SEQ ID NUMBERS (SEQUENCE LISTING):

| SEQ ID NO | Sequence | Remarks |
| --- | --- | --- |
| SEQ ID NO: 1 | WLPFGFILI | IL13RA2 epitope, IL13RA2-H |
| SEQ ID NO: 2 | LLDTNYNLF | IL13RA2 epitope |
| SEQ ID NO: 3 | CLYTFLIST | IL13RA2 epitope |
| SEQ ID NO: 4 | FLISTTFGC | IL13RA2 epitope |
| SEQ ID NO: 5 | VLLDTNYNL | IL13RA2 epitope |
| SEQ ID NO: 6 | YLYTFLIST | Sequence variant |
| SEQ ID NO: 7 | KLYTFLISI | Sequence variant |
| SEQ ID NO: 8 | CLYTFLIGV | Sequence variant |
| SEQ ID NO: 9 | FLISTTFTI | Sequence variant |
| SEQ ID NO: 10 | FLISTTFAA | Sequence variant |
| SEQ ID NO: 11 | TLISTTFGV | Sequence variant |
| SEQ ID NO: 12 | KLISTTFGI | Sequence variant |
| SEQ ID NO: 13 | NLISTTFGI | Sequence variant |
| SEQ ID NO: 14 | FLISTTFAS | Sequence variant |
| SEQ ID NO: 15 | VLLDTNYEI | Sequence variant |
| SEQ ID NO: 16 | ALLDTNYNA | Sequence variant |
| SEQ ID NO: 17 | ALLDTNYNA | Sequence variant |
| SEQ ID NO: 18 | FLPFGFILV | Sequence variant, IL13RA2-B |
| SEQ ID NO: 19 | QYTNVKYPFPYDPPYVPNENPTGLYHQKFHLS KEQKQYQQFLNFEGVDSCFYLYVNKTFVGYS QVSHSTSEFDITPFTVEGQNELHVIVLKWCDG SYLEDQDKFRMSGIFRDVYLMFRPENYVWDY NIRTSLSNENSKAKIEVFIMNQGQLKNPHYQL LNSEGIVLWEQYTKDTSFQFEVSNPILWNAEA PYLYTFLISTEEEVIVQQLGIREVSISEGVLLING KPIKLKGVNRHDMDPVTGFTISYEQAKKDMT LMKEHNINAIRTSHYPNAPWFPILCNEYGFYVI AEADLEAHGAVSFYGGGYDKTYGDIVQRPMF YEAILDRNERNLMRDKNNPSIFMWSMGNEAG YSKAFEDTGRYLKELDPTRLVHYEGSIHETGG HKNDTSMIDVFSRMYASVDEIRDYLSKPNKKP | Bacterial protein |

TABLE OF SEQUENCES AND SEQ ID NUMBERS (SEQUENCE LISTING):

| SEQ ID NO | Sequence | Remarks |
|---|---|---|
| | FVLCEFIHAMGNGPGDIEDYLSLFYEMDRIAG<br>GFVWEWSDHGIYMGKTEEGIKKYYYGDDFDI<br>YPNDSNFCVDGLTSPDRIPHQGLLEYKNAIRPI<br>RAALKSAIYPYEVTLINCLDFTNAKDLVELNIE<br>LLKNGEVVANQRVECPDIPPRCSTNIKIDYPHF<br>KGVEWQEGDYVHINLTYLQKVAKPLTPRNHS<br>LGFDQLLVNEPSRKEFWSVGNEFDIQNRTPID<br>NNEEISIEDLGNKIQLHHTNFHYVYNKFTGLFD<br>SIVWNQKSRLTKPMEFNIWRALIDNDKKHAD<br>DWKAAGYDRALVRVYKTSLTKNPDTGGIAIV<br>SEFSLTAVHIQRILEGSIEWNIDRDGVLTFHVD<br>AKRNLSMPFLPRFGIRCFLPSAYEEVSYLGFGP<br>RESYIDKHRASYFGQFHNLVERMYEDNIKPQE<br>NSSHCGCRFVSLQNNAKDQIYVASKEAFSFQA<br>SRYTQEELEKKRHNYELVKDEDTILCLDYKM<br>SGIGSAACGPELAEQYQLKEEEIKFSLQIRFDR | |
| SEQ ID NO: 20 | MKTIRKLYTFLISIFVILSLCSCYNDTHIITWQN<br>EDGTILAVDEVANGQIPVFQGSTPTKDSSSQYE<br>YSE | Bacterial protein |
| SEQ ID NO: 21 | MATLYCLYTFLIGVLYHSAWFLTQAFYYLLLF<br>LIRLILSHQIRTSCNSSPLTRLKTCLMIGWLLLL<br>FTPILSGMTILIPHQESSTTHFSQNVLLVVALYT<br>FINLGNVLRGFAKPRRATVLLKTDKNVVMVT<br>MMTSLYNLQTLMLAAYSHDKSYTQLMTMTT<br>GLVIIVITIGLALWMIIESRHKIKQLANNAG | Bacterial protein |
| SEQ ID NO: 22 | ICAKNNGNPNTSSTNYAFLISTTFTINKGFVDV<br>YSELNHALYSYDTVTFSGGTIIARTGSSASSSY<br>RPIRLGLNSSNPIVINAPTFTLDLSKQSDGSAM<br>TTYSDVSNDKVKTLLAASGSSANHYAKLTSEF<br>PPTVSTSTTGSGVTVSVKTDGQQQYLFIARYD<br>STGHLLELQQRLRGEEAILKAEFTFPTVSPT | Bacterial protein |
| SEQ ID NO: 23 | MEHKRKKQWILIIMLLLTVCSVFVVYAGREW<br>MFTNPFKPYTFSSVSYASGDGDGCTYVIDDSN<br>RKILKISADGRLLWRACASDKSFLSAERVVAD<br>GDGNVYLHDVRIEQGVQIASEGIVKLSSKGKY<br>ISTVASVEAEKGSVRRNIVGMVPTEHGVVYM<br>QKEKEGILVSNTEQGSSKVFSVADAQDRILCC<br>AYDRDSDSLFYVTYDGKIYKYTDSGQDELLY<br>DSDTVDGSIPQEISYSDGVLYSADIGLRDIIRIP<br>CDMENTGSTDRLTVEESLKEREIAYHVSAPGT<br>LVSSTNYSVILWDGEDYEQFWDVPLSGKLQV<br>WNCLLWAACAVIVAAVLFFAVTLLKILVKKF<br>SFYAKITMAVIGIIVGVAALFIGTLFPQFQSLLV<br>DETYTREKFAASAVTNRLPADAFQRLEKPSDF<br>MNEDYRQVRQVVRDVFFSDSDSSQDLYCVLY<br>KVKDGTVTLVYTLEDICVAYPYDWEYEGTDL<br>QEVMEQGATKTYATNSSAGGFVFIHSPIRDKS<br>GDIIGIIEVGTDMNSLTEKSREIQVSLIINLIAIM<br>VVFFMLTFEVIYFIKGRQELKRRKQEEDNSRLP<br>VEIFRFIVFLVFFFTNLTCAILPIYAMKISEKMS<br>VQGLSPAMLAAVPISAEVLSGAIFSALGGKVIH<br>KLGAKRSVFVSSVLLTAGLGLRVVPNIWLLTL<br>SALLLGAGWGVLLLLVNLMIVELPDEEKNRA<br>YAYYSVSSLSGANCAVVFGGFLLQWMSYTAL<br>FAVTAVLSVLLFLVANKYMSKYTSDNEEENC<br>ETEDTHMNIVQFIFRPRIISFFLLMMIPLLICGYF<br>LNYMFPIVGSEWGLSETYIGYTYLLNGIFVLIL<br>GTPLTEFFSNRGWKHLGLAVAAFIYAAAFLEV<br>TMLQNIPSLLIALALIGVADSFGIPLLTSYFTDL<br>KDVERFGYDRGLGVYSLFENGAQSLGSFVFG<br>YVLVLGVGRGLIFVLILVSVLSAAFLISTTFAA<br>RDKRRSKNMEKRRKLNVELIKFLIGSMLVV<br>GVLMLLGSSLVNNRQYRKLYNDKALEIAKTV<br>SDQVNGDFIEELCKEIDTEEFEQIQKEAVAADD<br>EQPIIDWLKEKGMYQNYERINEYLHSIQADMN<br>IEYLYIQMIQDHSSVYLFDPSSGYLTLGYKEEL<br>SERFDKLKGNERLEPTVSRTEFGWLSSAGEPV<br>LSSDGEKCAVAFVDIDMTEIVRNTIRFTVLMV | Bacterial protein |

TABLE OF SEQUENCES AND SEQ ID NUMBERS (SEQUENCE LISTING):

| SEQ ID NO | Sequence | Remarks |
|---|---|---|
| | CLCILIILAAGMDISRKIKKRISRPIELLTEATHK FGNGEEGYDENNIVDLDIHTRDEIEELYHATQS MQKSIINYMDNLTRVTAEKERIGAELNVATQI QASMLPCIFPAFPDRDEMDIYATMTPAKEVGG DFYDFFMVDDRHMAIVMADVSGKGVPAALF MVIGKTLIKDHTQPGRDLGEVFTEVNNILCES NENGMFITAFEGVLDLVTGEFRYVNAGHEMP FVYRRETNTYEAYKIRAGFVLAGIEDIVYKEQ KLQLNIGDKIFQYTDGVTEATDKDRQLYGMD RLDHVLNQQCLSSNPEETLKLVKADIDAFVGD NDQFDDITMLCLEYTKKMENQRLLNNC | |
| SEQ ID NO: 24 | MAACAACRWLMNEKTLISTTFGVGQLTLNAV EHKAKQDCY | Bacterial protein |
| SEQ ID NO: 25 | MAKLNIGIFTDTYFPQLNGVATSVQTLRRELE KRGHQVYIFTPYDPRQQQETDDHIFRLPSMPFI FVKNYRACFVCPPHILRKIHQLKLDIIHTQTEFS LGFLGKLISTTFGIPMVHTYHTMYEDYVHYIA GGHLISAEGAREFSRIFCNTAMAVIAPTQKTER LLLSYGVNKPISIIPTGIDTSHFRKSNYDPAEILE LRHSLGLKADTPVLISIGRIAKEKSIDVIIGALP KLLEKLPNTMMVIVGEGMEIENLKKYADSLGI GDHLLFTGGKPWSEIGKYYQLGDVFCSASLSE TQGLTFAEAMAGGIPVVARRDDCIVNFMTHG ETGMFFDDPAELPDLLYRVLTDKPLREHLSTT SQNTMESLSVETFGNHVEELYEKVVRAFQNA ESIPLHSLPYIKGTRVVHRISKIPKKLAHRSRSY SSQIAERLPFLPRHRS | Bacterial protein |
| SEQ ID NO: 26 | MIILNAMKLINLISTTFGIGVQDLLLKESFNEVE VCFRLPRPFCVIADDINLFYAQILDDCQFDFLY CGNSEITINSLHSITDVENFVSHISDKLASLDLN DPDDIEVVNSFSILVKIRKEIRERVLNIYDFIAL CNYWNDLTWENRLFVLSKEELKRGIVFYLLE DDICSFKTEGFYFSHNREEKPHIVNCLEDIREN VYWGNLDVYKLTPLYFHITQRSNVENIFQETF DVLSAVFSLCSILDIVSLNAKDGKLVYKLCGY KNINGELNIDNSFSLLKNTENEYFKIFRWIYIGE GNKTDKIGIARNVLSLFIANDNIAIEDNVFISIQ SSFKTYLKENLDKYVAIRNQIYQELDAIISLSS AVKKDFLEGFKHNLLACITFFFSTIVLEVLGGN SKSYFLFTKEVCILCYAVFFISFLYLLWMRGDI EVEKKNISNRYVVLKKRYSDLLIPKEIDIILRN GEELKEQMGYIDLVKKKYTALWICSLLTLCVI VTVLSPIGNMFAGMIFAFKSIIVIFGLLIFLLVRL GSFIL | Bacterial protein |
| SEQ ID NO: 27 | MNVFAGIQFGIRKGLRYKVNTYSWFLADLAL YASVILMYFLISTTFASFGAYTKTEMGLYISTY FIINNLFAVLFSEAVSEYGASILNGSFSYYQLTP VGPLRSLILLNFNFAAMLSTPALLAMNIYFVV QLFTTPVQVILYYLGVLFACGTMLFVFQTISAL LLFGVRSSAIASAMTQLFSIAEKPDMVFHPAFR KVFTFVIPAFLFSAVPSKVMLGTAAVSEIAALF LSPLFFYALFRILEAAGCRKYQHAGF | Bacterial protein |
| SEQ ID NO: 28 | MNKALFKYFATVLIVTLLFSSSVSMVILSDQM MQTTRKDMYYTVKLVENQIDYQKPLDNQVE KLNDLAYTKDTRLTIIDKDGNVLADSDKEGIQ ENHSGRSEFKEALSDQFGYATRYSSTVKKNM MYVAYYHRGYVVRIAIPYNGIFDNIGPLLEPLF ISAALSLCVALALSYRFSRTLTKPLEEISEEVSK INDNRYLSFDHYQYDEFNVIATKLKEQADTIR KTLKTLKNERLKINSILDKMNEGFVLLDTNYEI LMVNKKAKQLFGDKMEVNQPIQDFIFDHQIID QLENIGVEPKIVTLKKDEEVYDCHLAKVEYGV TLLFVNITDSVNATKMRQEFFSNVSHELKTPM TSIRGYSELLQTGMIDDPKARKQALDKIQKEV DQMSSLISDILMISRLENKDIEVIQHPVHLQPIV DDILESLKVEIEKKEIKVTCDLTPQTYLANHQH | Bacterial protein |

| SEQ ID NO | Sequence | Remarks |
|---|---|---|
| | VQQLMNNLINNAVKYNKQKGSLNIHSYLVDQ DYIIEVSDTGRGISLIDQGRVFERFFRCDAGRD KETGGTGLGLAIVKHIVQYYKGTIHLESELGK GTTFKIVLPINKDSL | |
| SEQ ID NO: 29 | MSISLAEAKVGMADKVDQQVVDEFRRASLLL DMLIFDDAVSPGTGGSTLTYGYTCLKTPSTVA VRELNTEYTPNEAKREKKTADLKIFGGSYQID RVIAQTSGAVNEVEFQMREKIKAAANYFHML VINGTGAGSGAGYVTNTFDGLKKILSGSDTEY TAEDVDISTSALLDTNYNAFLDAVDTFISKLAE KPDILMMNTEMLTKVRSAARRAGYYDRSKD DFGRAVETYNGIKLLDAGYYYNGSTTEPVVAI ETDGSTAIYGIKIGLNAFHGVSPKGDKIIAQHL PDFSQAGAVKEGDVEMVAATVLKNSKMAGV LKGIKIKPTE | Bacterial protein |
| SEQ ID NO: 30 | MPVTLAEAKVGMADKVDQQVIDEFRRSSLLL DMLTFDDSVSPGTGGSTLTYGYVRLKTPSTVA VRSINSEYTANEAKREKATANVIILGGSFEVDR VIANTSGAVDEIDFQLKEKTKAGANYFHNLVI NGTSAASGAGFVVNTFDGLKKILSGSDTEYTS ESDISTSALLDTNYNAFLDELDAFISKLAEKPDI LLMNNEMLTKTRAAARRAGFYERSVDGFGRT VEKYNGIPMMDAGQYYNGSATVDVIETSTPS TSAYGETDIYAVKLGLNAFHGISVDGSKMIHT YLPDLQAPGAVKKGKVELLAGAILKNSKMAG RLKGIKIKPKTTAGG | Bacterial protein |
| SEQ ID NO: 31 | MVFVFSLLFSPFFALFFLLLYLRYKIKKIHVA LSVFLVAFIGIYWYPWGDNQTHFAIYYLDIVN NYYSLALSSSHWLYDVVIYHIASLTGQYIWGY YFWLFVPFLFFSLLVWQIVDEQEVPNKEKWLL LILLILFLGIRELLDLNRNTNAGLLLAIATLLWQ KNKALSITCVIVSLLLHDSVRYFIPFLPFGFILV KQSQRKTDLIIITTIIISGFLIKVIAPLVVSERNA MYLEVGGGRGVGSFMVLQGYVNILIGIIQYL IIRRNKSVIAKPLYVVYIVSILIAAALSSMWVG RERFLLVSNILATSIILTSWSKLRLVEGVKVLR NFQLIIGSYSMKIIINLLLVYSAHYVFNSATTDN QKEFSIVARSFYMPTFMLFDIENYGFSDKKFM NLYDRVDSTIDGE | Bacterial protein |
| SEQ ID NO: 32 | MAKTIAYDEEARRGLERGLN | HHD-DR3 |

The invention claimed is:

1. A medicament comprising a human microbiota peptide sequence variant of a human tumor-related antigenic epitope sequence, wherein the human microbiota peptide sequence variant comprises or consists of an amino acid sequence according to any one of SEQ ID NOs: 6-16.

2. The medicament according to claim 1, wherein the medicament comprises a nanoparticle loaded with the human microbiota peptide sequence variant.

3. The medicament according to claim 2, wherein the nanoparticle is further loaded with an adjuvant.

4. The medicament according to claim 1, wherein the medicament comprises a bacterial cell expressing the human microbiota peptide sequence variant.

5. The medicament according to claim 1, wherein the medicament comprises:
  (i) a recombinant protein comprising the human microbiota peptide sequence variant;
  (ii) an immunogenic compound comprising the human microbiota peptide sequence variant;
  (iii) a nanoparticle loaded with the human microbiota peptide sequence variant;

(iv) an antigen-presenting cell loaded with the human microbiota peptide sequence variant;

(v) a host cell expressing the human microbiota peptide sequence variant; or (vi) a nucleic acid molecule encoding the human microbiota peptide sequence variant;

and, optionally, a pharmaceutically acceptable carrier and/or an adjuvant.

6. The medicament according to claim 1, wherein the medicament is a vaccine.

7. A method for treating a cancer or initiating, enhancing or prolonging an anti-tumor response in a subject in need thereof, the method comprising administering to the subject the medicament according to claim 1.

8. The method according to claim 7, wherein the medicament is administered in combination with an anti-cancer agent.

9. The method according to claim 7, further comprising a step of determining whether the human microbiota peptide sequence variant of the tumor-related antigenic epitope sequence is present in the subject.

10. The method according to claim 8, wherein the anti-cancer agent is an immune checkpoint modulator.

11. The method according to claim 10, wherein the immune checkpoint modulator is CD40, LAG3, CTLA4, PD-L1, PD-L2, PD-1 and/or IDO.

12. The method according to claim 9, wherein the determining step comprises determining whether the human microbiota peptide sequence variant of the tumor-related antigenic epitope sequence is present in a stool sample or a blood sample of the subject.

13. The method according to claim 7, wherein the medicament is administered to the subject by subcutaneous, oral or intranodal administration.

14. The medicament according to claim 1, further comprising an adjuvant.

* * * * *

SEQUENCE LISTING

```
Sequence total quantity: 32
SEQ ID NO: 1          moltype = AA  length = 9
FEATURE               Location/Qualifiers
source                1..9
                      mol_type = protein
                      organism = Homo sapiens
SEQUENCE: 1
WLPFGFILI                                                               9

SEQ ID NO: 2          moltype = AA  length = 9
FEATURE               Location/Qualifiers
source                1..9
                      mol_type = protein
                      organism = Homo sapiens
SEQUENCE: 2
LLDTNYNLF                                                               9

SEQ ID NO: 3          moltype = AA  length = 9
FEATURE               Location/Qualifiers
source                1..9
                      mol_type = protein
                      organism = Homo sapiens
```

```
SEQUENCE: 3
CLYTFLIST                                                                                    9

SEQ ID NO: 4           moltype = AA  length = 9
FEATURE                Location/Qualifiers
source                 1..9
                       mol_type = protein
                       organism = Homo sapiens
SEQUENCE: 4
FLISTTFGC                                                                                    9

SEQ ID NO: 5           moltype = AA  length = 9
FEATURE                Location/Qualifiers
source                 1..9
                       mol_type = protein
                       organism = Homo sapiens
SEQUENCE: 5
VLLDTNYNL                                                                                    9

SEQ ID NO: 6           moltype = AA  length = 9
FEATURE                Location/Qualifiers
REGION                 1..9
                       note = sequence variant
source                 1..9
                       mol_type = protein
                       organism = synthetic construct
SEQUENCE: 6
YLYTFLIST                                                                                    9

SEQ ID NO: 7           moltype = AA  length = 9
FEATURE                Location/Qualifiers
REGION                 1..9
                       note = sequence variant
source                 1..9
                       mol_type = protein
                       organism = synthetic construct
SEQUENCE: 7
KLYTFLISI                                                                                    9

SEQ ID NO: 8           moltype = AA  length = 9
FEATURE                Location/Qualifiers
REGION                 1..9
                       note = sequence variant
source                 1..9
                       mol_type = protein
                       organism = synthetic construct
SEQUENCE: 8
CLYTFLIGV                                                                                    9

SEQ ID NO: 9           moltype = AA  length = 9
FEATURE                Location/Qualifiers
REGION                 1..9
                       note = sequence variant
source                 1..9
                       mol_type = protein
                       organism = synthetic construct
SEQUENCE: 9
FLISTTFTI                                                                                    9

SEQ ID NO: 10          moltype = AA  length = 9
FEATURE                Location/Qualifiers
REGION                 1..9
                       note = sequence variant
source                 1..9
                       mol_type = protein
                       organism = synthetic construct
SEQUENCE: 10
FLISTTFAA                                                                                    9

SEQ ID NO: 11          moltype = AA  length = 9
FEATURE                Location/Qualifiers
REGION                 1..9
                       note = sequence variant
source                 1..9
                       mol_type = protein
                       organism = synthetic construct
SEQUENCE: 11
TLISTTFGV                                                                                    9
```

```
SEQ ID NO: 12           moltype = AA   length = 9
FEATURE                 Location/Qualifiers
REGION                  1..9
                        note = sequence variant
source                  1..9
                        mol_type = protein
                        organism = synthetic construct
SEQUENCE: 12
KLISTTFGI                                                                  9

SEQ ID NO: 13           moltype = AA   length = 9
FEATURE                 Location/Qualifiers
REGION                  1..9
                        note = sequence variant
source                  1..9
                        mol_type = protein
                        organism = synthetic construct
SEQUENCE: 13
NLISTTFGI                                                                  9

SEQ ID NO: 14           moltype = AA   length = 9
FEATURE                 Location/Qualifiers
REGION                  1..9
                        note = sequence variant
source                  1..9
                        mol_type = protein
                        organism = synthetic construct
SEQUENCE: 14
FLISTTFAS                                                                  9

SEQ ID NO: 15           moltype = AA   length = 9
FEATURE                 Location/Qualifiers
REGION                  1..9
                        note = sequence variant
source                  1..9
                        mol_type = protein
                        organism = synthetic construct
SEQUENCE: 15
VLLDTNYEI                                                                  9

SEQ ID NO: 16           moltype = AA   length = 9
FEATURE                 Location/Qualifiers
REGION                  1..9
                        note = sequence variant
source                  1..9
                        mol_type = protein
                        organism = synthetic construct
SEQUENCE: 16
ALLDTNYNA                                                                  9

SEQ ID NO: 17           moltype = AA   length = 9
FEATURE                 Location/Qualifiers
REGION                  1..9
                        note = sequence variant
source                  1..9
                        mol_type = protein
                        organism = synthetic construct
SEQUENCE: 17
ALLDTNYNA                                                                  9

SEQ ID NO: 18           moltype = AA   length = 9
FEATURE                 Location/Qualifiers
REGION                  1..9
                        note = sequence variant
source                  1..9
                        mol_type = protein
                        organism = synthetic construct
SEQUENCE: 18
FLPFGFILV                                                                  9

SEQ ID NO: 19           moltype = AA   length = 930
FEATURE                 Location/Qualifiers
REGION                  1..930
                        note = bacterial protein
source                  1..930
                        mol_type = protein
                        organism = synthetic construct
SEQUENCE: 19
QYTNVKYPFP YDPPYVPNEN PTGLYHQKFH LSKEQKQYQQ FLNFEGVDSC FYLYVNKTFV          60
```

```
GYSQVSHSTS EFDITPFTVE GQNELHVIVL KWCDGSYLED QDKFRMSGIF RDVYLMFRPE  120
NYVWDYNIRT SLSNENSKAK IEVFIMNQGQ LKNPHYQLLN SEGIVLWEQY TKDTSFQFEV  180
SNPILWNAEA PYLYTFLIST EEEVIVQQLG IREVSISEGV LLINGKPIKL KGVNRHDMDP  240
VTGFTISYEQ AKKDMTLMKE HNINAIRTSH YPNAPWFPIL CNEYGFYVIA EADLEAHGAV  300
SFYGGGYDKT YGDIVQRPMF YEAILDRNER NLMRDKNNPS IFMWSMGNEA GYSKAFEDTG  360
RYLKELDPTR LVHYEGSIHE TGGHKNDTSM IDVFSRMYAS VDEIRDYLSK PNKKPFVLCE  420
FIHAMGNGPG DIEDYLSLFY EMDRIAGGFV WEWSDHGIYM GKTEEGIKKY YYGDDFDIYP  480
NDSNFCVDGL TSPDRIPHQG LLEYKNAIRP IRAALKSAIY PYEVTLINCL DFTNAKDLVE  540
LNIELLKNGE VVANQRVECP DIPPRCSTNI KIDYPHFKGV EWQEGDYVHI NLTYLQKVAK  600
PLTPRNHSLG FDQLLVNEPS RKEFWSVGNE FDIQNRTPID NNEEISIEDL GNKIQLHHTN  660
FHYVYNKFTG LFDSIVWNQK SRLTKPMEFN IWRALIDNDK KHADDWKAAG YDRALVRVYK  720
TSLTKNPDTG GIAIVSEFSL TAVHIQRILE GSIEWNIDRD GVLTFHVDAK RNLSMPFLPR  780
FGIRCFLPSA YEEVSYLGFG PRESYIDKHR ASYFGQFHNL VERMYEDNIK PQENSSHCGC  840
RFVSLQNNAK DQIYVASKEA FSFQASRYTQ EELEKKRHNY ELVKDEDTIL CLDYKMSGIG  900
SAACGPELAE QYQLKEEEIK FSLQIRFDRS                                  930

SEQ ID NO: 20           moltype = AA  length = 70
FEATURE                 Location/Qualifiers
REGION                  1..70
                        note = bacterial protein
source                  1..70
                        mol_type = protein
                        organism = synthetic construct
SEQUENCE: 20
MKTIRKLYTF LISIFVILSL CSCYNDTHII TWQNEDGTIL AVDEVANGQI PVFQGSTPTK   60
DSSSQYEYSF                                                         70

SEQ ID NO: 21           moltype = AA  length = 192
FEATURE                 Location/Qualifiers
REGION                  1..192
                        note = bacterial protein
source                  1..192
                        mol_type = protein
                        organism = synthetic construct
SEQUENCE: 21
MATLYCLYTF LIGVLYHSAW FLTQAFYYLL LFLIRLILSH QIRTSCNSSP LTRLKTCLMI   60
GWLLLLFTPI LSGMTILIPH QESSTTHFSQ NVLLVVALYT FINLGNVLRG FAKPRRATVL  120
LKTDKNVVMV TMMTSLYNLQ TLMLAAYSHD KSYTQLMTMT TGLVIIVITI GLALWMIIES  180
RHKIKQLANN AG                                                     192

SEQ ID NO: 22           moltype = AA  length = 194
FEATURE                 Location/Qualifiers
REGION                  1..194
                        note = bacterial protein
source                  1..194
                        mol_type = protein
                        organism = synthetic construct
SEQUENCE: 22
ICAKNNGNPN TSSTNYAFLI STTFTINKGF VDVYSELNHA LYSYDTVTFS GGTIIARTGS   60
SASSSYRPIR LGLNSSNPIV INAPTFTLDL SKQSDGSAMT TYSDVSNDKV KTLLAASGSS  120
ANHYAKLTSE FPPTVSTSTT GSGVTVSVKT DGQQQYLFIA RYDSTGHLLE LQQRLRGEEA  180
ILKAEFTFPT VSPT                                                   194

SEQ ID NO: 23           moltype = AA  length = 1538
FEATURE                 Location/Qualifiers
REGION                  1..1538
                        note = bacterial protein
source                  1..1538
                        mol_type = protein
                        organism = synthetic construct
SEQUENCE: 23
MEHKRKKQWI LIIMLLLTVC SVFVVYAGRE WMFTNPFKPY TFSSVSYASG DGDGCTYVID   60
DSNRKILKIS ADGRLLWRAC ASDKSFLSAE RVVADGDGNV YLHDVRIEQG VQIASEGIVK  120
LSSKGKYIST VASVEAEKGS VRRNIVGMVP TEHGVVYMQK EKEGILVSNT EQGSSKVFSV  180
ADAQDRILCC AYDRDSDSLF YVTYDGKIYK YTDSGQDELL YDSDTVDGSI PQEISYSDGV  240
LYSADIGLRD IIRIPCDMEN TGSTDRLTVE ESLKEREIAY HVSAPGTLVS STNYSVILWD  300
GEDYEQFWDV PLSGKLQVWN CLLWAACAVI VAAVLFFAVT LLKILVKKFS FYAKITMAVI  360
GIIVGVAALF IGTLFPQFQS LLVDETYTRE KFAASAVTNR LPADAFQRLE KPSDFMNEDY  420
RQVRQVVRDV FFSDSDSSQD LYCVLYKVKD GTVTLVYTLE DICVAYPYDW EYEGTDLQEV  480
MEQGATKTYA TNSSAGGFVF IHSPIRDKSG DIIGIIEVGT DMNSLTEKSR EIQVSLIINL  540
IAIMVVFFML TFEVIYFIKG RQELKRRKQE EDNSRLPVEI FRFIVFLVFF FTNLTCAILP  600
IYAMKISEKM SVQGLSPAML AAVPISAEVL SGAIFSALGG KVIHKLGAKR SVFVSSVLLT  660
AGLGLRVVPN IWLLTSALL LGAGWGVLLL LVNLMIVELP DEEKNRAYAY YSVSSLSGAN  720
CAVVFGGFLL QWMSYTALFA VTAVLSVLLF LVANKYMSKY TSDNEEENCE TEDTHMNIVQ  780
FIFRPRIISF FLLMMIPLLI CGYFLNYMFP IVGSEWGLSE TYIGYTYLLN GIFVLILGTP  840
LTEFFSNRGW KHLGLAVAAF IYAAAFLEVT MLQNIPSLLI ALALIGVADS FGIPLLTSYF  900
TDLKDVERFG YDRGLGVYSL FENGAQSLGS FVFGYVLVLG VGRGLIFVLI LVSVLSAAFL  960
ISTTFAAHRD KRRSKNMEKR RKLNVELIFK LIGSMLVVGV LMLLGSSLVN NRQYRKLYND 1020
KALEIAKTVS DQVNGDFIEE LCKEIDTEEF EQIQKEAVAA DDEQPIIDWL KEKGMYQNYE 1080
```

```
RINEYLHSIQ ADMNIEYLYI QMIQDHSSVY LFDPSSGYLT LGYKEELSER FDKLKGNERL   1140
EPTVSRTEFG WLSSAGEPVL SSDGEKCAVA FVDIDMTEIV RNTIRFTVLM VCLCILIILA   1200
AGMDISRKIK KRISRPIELL TEATHKFGNG EEGYDENNIV DLDIHTRDEI EELYHATQSM   1260
QKSIINYMDN LTRVTAEKER IGAELNVATQ IQASMLPCIF PAFPDRDEMD IYATMTPAKE   1320
VGGDFYDFFM VDDRHMAIVM ADVSGKGVPA ALFMVIGKTL IKDHTQPGRD LGEVFTEVNN   1380
ILCESNENGM FITAFEGVLD LVTGEFRYVN AGHEMPFVYR RETNTYEAYK IRAGFVLAGI   1440
EDIVYKEQKL QLNIGDKIFQ YTDGVTEATD KDRQLYGMDR LDHVLNQQCL SSNPEETLKL   1500
VKADIDAFVG DNDQFDDITM LCLEYTKKME NQRLLNNC                          1538

SEQ ID NO: 24           moltype = AA  length = 40
FEATURE                 Location/Qualifiers
REGION                  1..40
                        note = bacterial protein
source                  1..40
                        mol_type = protein
                        organism = synthetic construct
SEQUENCE: 24
MAACAACRWL MNEKTLISTT FGVGQLTLNA VEHKAKQDCY                         40

SEQ ID NO: 25           moltype = AA  length = 441
FEATURE                 Location/Qualifiers
REGION                  1..441
                        note = bacterial protein
source                  1..441
                        mol_type = protein
                        organism = synthetic construct
SEQUENCE: 25
MAKLNIGIFT DTYFPQLNGV ATSVQTLRRE LEKRGHQVYI FTPYDPRQQQ ETDDHIFRLP   60
SMPFIFVKNY RACFVCPPHI LRKIHQLKLD IIHTQTEFSL GFLGKLISTT FGIPMVHTYH   120
TMYEDVHYI AGGHLISAEG AREFSRIFCN TAMAVIAPTQ KTERLLLSYG VNKPISIIPT   180
GIDTSHFRKS NYDPAEILEL RHSLGLKADT PVLISIGRIA KEKSIDVIIG ALPKLLEKLP   240
NTMMVIVGEG MEIENLKKYA DSLGIGDHLL FTGGKPWSEI GKYYQLGDVF CSASLSETQG   300
LTFAEAMAGG IPVVARRDDC IVNFMTHGET GMFFDDPAEL PDLLYRVLTD KPLREHLSTT   360
SQNTMESLSV ETFGNHVEEL YEKVVRAFQN AESIPLHSLP YIKGTRVVHR ISKIPKKLAH   420
RSRSYSSQIA ERLPFLPRHR S                                            441

SEQ ID NO: 26           moltype = AA  length = 535
FEATURE                 Location/Qualifiers
REGION                  1..535
                        note = bacterial protein
source                  1..535
                        mol_type = protein
                        organism = synthetic construct
SEQUENCE: 26
MIILNAMKLI NLISTTFGIG VQDLLLKESF NEVEVCFRLP RPFCVIADDI NLFYAQILDD   60
CQFDFLYCGN SEITINSLHS ITDVENFVSH ISDKLASLDL NDPDDIEVVN SFSILVKIRK   120
EIRERVLNIY DFIALCNYWN DLTWENRLFV LSKEELKRGI VFYLLEDDIC SFKTEGFYFS   180
HNREEKPHIV NCLEDIRENV YWGNLDVYKL TPLYFHITQR SNVENIFQET FDVLSAVFSL   240
CSILDIVSLN AKDGKLVYKL CGYKNINGEL NIDNSFSLLK NTENEYFKIF RWIYIGEGNK   300
TDKIGIARNV LSLFIANDNI AIEDNVFISI QSSFKTYLKE NLDKYVAIRN QIYQELDAII   360
SLSSAVKKDF LEGFKHNLLA CITFFFSTIV LEVLGGNSKS YLFLFTKEVCI LCYAVFFISF   420
LYLLWMRGDI EVEKKNISNR YVVLKKRYSD LLIPKEIDII LRNGEELKEQ MGYIDLVKKK   480
YTALWICSLL TLCVIVTVLS PIGNMFAGMI FAFKSIIVIF GLLIFLLVRL GSFIL        535

SEQ ID NO: 27           moltype = AA  length = 255
FEATURE                 Location/Qualifiers
REGION                  1..255
                        note = bacterial protein
source                  1..255
                        mol_type = protein
                        organism = synthetic construct
SEQUENCE: 27
MNVFAGIQFG IRKGLRYKVN TYSWFLADLA LYASVILMYF LISTTFASFG AYTKTEMGLY   60
ISTYFIINNL FAVLFSEAVS EYGASILNGS FSYYQLTPVG PLRSLILLNF NFAAMLSTPA   120
LLAMNIYFVV QLFTTPVQVI LYYLGVLFAC GTMLFVFQTI SALLLFGVRS SAIASAMTQL   180
FSIAEKPDMV FHPAFRKVFT FVIPAFLFSA VPSKVMLGTA AVSEIAALFL SPLFFYALFR   240
ILEAAGCRKY QHAGF                                                   255

SEQ ID NO: 28           moltype = AA  length = 563
FEATURE                 Location/Qualifiers
REGION                  1..563
                        note = bacterial protein
source                  1..563
                        mol_type = protein
                        organism = synthetic construct
SEQUENCE: 28
MNKALFKYFA TVLIVTLLFS SSVSMVILSD QMMQTTRKDM YYTVKLVENQ IDYQKPLDNQ   60
VEKLNDLAYT KDTRLTIIDK DGNVLADSDK EGIQENHSGR SEFKEALSDQ FGYATRYSST   120
VKKNMMYVAY YHRGYVVRIA IPYNGIFDNI GPLLEPLFIS AALSLCVALA LSYRFSRTLT   180
```

```
KPLEEISEEV SKINDNRYLS FDHYQYDEFN VIATKLKEQA DTIRKTLKTL KNERLKINSI    240
LDKMNEGFVL LDTNYEILMV NKKAKQLFGD KMEVNQPIQD FIFDHQIIDQ LENIGVEPKI    300
VTLKKDEEVY DCHLAKVEYG VTLLFVNITD SVNATKMRQE FFSNVSHELK TPMTSIRGYS    360
ELLQTGMIDD PKARKQALDK IQKEVDQMSS LISDILMISR LENKDIEVIQ HPVHLQPIVD    420
DILESLKVEI EKKEIKVTCD LTPQTYLANH QHVQQLMNNL INNAVKYNKQ KGSLNIHSYL    480
VDQDYIIEVS DTGRGISLID QGRVFERFFR CDAGRDKETG GTGLGLAIVK HIVQYYKGTI    540
HLESELGKGT TFKIVLPINK DSL                                           563

SEQ ID NO: 29          moltype = AA  length = 326
FEATURE                Location/Qualifiers
REGION                 1..326
                       note = bacterial protein
source                 1..326
                       mol_type = protein
                       organism = synthetic construct
SEQUENCE: 29
MSISLAEAKV GMADKVDQQV VDEFRRASLL LDMLIFDDAV SPGTGGSTLT YGYTCLKTPS     60
TVAVRELNTE YTPNEAKREK KTADLKIFGG SYQIDRVIAQ TSGAVNEVEF QMREKIKAAA    120
NYFHMLVING TGAGSGAGYV TNTFDGLKKI LSGSDTEYTA EDVDISTSAL LDTNYNAFLD    180
AVDTFISKLA EKPDILMMNT EMLTKVRSAA RRAGYYDRSK DDFGRAVETY NGIKLLDAGY    240
YYNGSTTEPV VAIETDGSTA IYGIKIGLNA FHGVSPKGDK IIAQHLPDFS QAGAVKEGDV    300
EMVAATVLKN SKMAGVLKGI KIKPTE                                        326

SEQ ID NO: 30          moltype = AA  length = 334
FEATURE                Location/Qualifiers
REGION                 1..334
                       note = bacterial protein
source                 1..334
                       mol_type = protein
                       organism = synthetic construct
SEQUENCE: 30
MPVTLAEAKV GMADKVDQQV IDEFRRSSLL LDMLTFDDSV SPGTGGSTLT YGYVRLKTPS     60
TVAVRSINSE YTANEAKREK ATANVIILGG SFEVDRVIAN TSGAVDEIDF QLKEKTKAGA    120
NYFHNLVING TSAASGAGFV VNTFDGLKKI LSGSDTEYTS ESDISTSALL DTNYNAFLDE    180
LDAFISKLAE KPDILMLNNE MLTKTRAAAR RAGFYERSVD GFGRTVEKYN GIPMMDAGQY    240
YNGSATVDVI ETSTPSTSAY GETDIYAVKL GLNAFHGISV DGSKMIHTYL PDLQAPGAVK    300
KGKVELLAGA ILKNSKMAGR LKGIKIKPKT TAGG                               334

SEQ ID NO: 31          moltype = AA  length = 409
FEATURE                Location/Qualifiers
REGION                 1..409
                       note = bacterial protein
source                 1..409
                       mol_type = protein
                       organism = synthetic construct
SEQUENCE: 31
MVFVFSLLFS PFFALFFLLL YLYRYKIKKI HVALSVFLVA FIGIYWYPWG DNQTHFAIYY     60
LDIVNNYYSL ALSSSHWLYD YVIYHIASLT GQYIWGYYFW LFVPFLFFSL LVWQIVDEQE    120
VPNKEKWLLL ILLILFLGIR ELLDLNRNTN AGLLLAIATL LWQKNKALSI TCVIVSLLLH    180
DSVRYFIPFL PFGFILVKQS QRKTDLIIIT TIIISGFLIK VIAPLVVSER NAMYLEVGGG    240
RGVGSGFMVL QGYVNILIGI IQYLIIRRNK SVIAKPLYVV YIVSILIAAA LSSMWVGRER    300
FLLVSNILAT SIILTSWSKL RLVEGVKVLR NFQLIIGSYS MKIIINLLLV YSAHYVFNSA    360
TTDNQKEFSI VARSFYMPTF MLFDIENYGF SDKKFMNLYD RVDSTIDGE               409

SEQ ID NO: 32          moltype = AA  length = 20
FEATURE                Location/Qualifiers
REGION                 1..20
                       note = HHD-DR3
source                 1..20
                       mol_type = protein
                       organism = synthetic construct
SEQUENCE: 32
MAKTIAYDEE ARRGLERGLN                                                20
```